United States Patent [19]
Tomioka et al.

[11] Patent Number: 5,075,488
[45] Date of Patent: Dec. 24, 1991

[54] SOIL DISEASE-CONTROLLING CYANO AND ESTER DERIVATIVES OF CYCLOPENTENYL AMINE

[75] Inventors: Hiroki Tomioka, Hyogo; Tadashi Ooishi, Toyonaka; Junya Takahashi, Hyogo; Mitsuru Sasaki, Toyonaka; Naonori Hirata, Sakai, all of Japan

[73] Assignee: Sumitomo Chemical Company, Limited, Osaka, Japan

[21] Appl. No.: 66,735

[22] Filed: Jun. 25, 1987

Related U.S. Application Data

[62] Division of Ser. No. 610,789, May 16, 1984, Pat. No. 4,709,052.

[30] Foreign Application Priority Data

| May 31, 1983 | [JP] | Japan | 58-97545 |
| Jun. 3, 1983 | [JP] | Japan | 58-99959 |
| Jun. 9, 1983 | [JP] | Japan | 58-103949 |
| Jun. 13, 1983 | [JP] | Japan | 58-106233 |
| Aug. 17, 1983 | [JP] | Japan | 58-150853 |
| Aug. 18, 1983 | [JP] | Japan | 58-151117 |

[51] Int. Cl.$^5$ ............ C07C 121/48; C07C 87/451; C07C 87/452

[52] U.S. Cl. .............. 558/408; 560/125; 564/1; 548/548

[58] Field of Search .......... 558/408; 560/125; 564/1

[56] References Cited

U.S. PATENT DOCUMENTS

| 2,311,281 | 2/1943 | Roblin et al. | 564/105 |
| 2,390,597 | 12/1945 | Law et al. | 564/392 |
| 3,268,524 | 8/1966 | Moore et al. | 564/461 |

FOREIGN PATENT DOCUMENTS 0130552 7/1985 Japan .................. 564/1

OTHER PUBLICATIONS

Beilsteins Hand. der Organ. Chemie Syst#1595 in Hauptwerke & Er. I, Er. II, Er. III.

Primary Examiner—David B. Springer
Attorney, Agent, or Firm—Wenderoth, Lind & Ponack

[57] ABSTRACT

A soil disease controlling agent for preventing and controlling diseases caused by pathogenic fungi living in soil, which comprises an effective amount of at least one of a 2-cycloalkenylamine derivative and its salts as an active ingredient, and at least one inert carrier or diluent.

3 Claims, No Drawings

SOIL DISEASE-CONTROLLING CYANO AND ESTER DERIVATIVES OF CYCLOPENTENYL AMINE

This is a Rule 60 divisional application of Ser. No. 610,789, filed May 16, 1984, U.S. Pat. No. 4,709,052.

The present invention relates to a 2-cycloalkenylamine derivative and its salts which are soil disease-controlling agents, and production thereof. The 2-cycloalkenylamine derivative and its salt which are the active ingredient of the present invention, have excellent controlling effect against soil diseases caused by plant pathogens. More particularly, the present invention relates to a soil disease-controlling agent containing as an active ingredient a 2-cycloalkenylamine derivative or its salts (hereinafter referred to as present compound), a novel 2-cycloalkenylamine derivative and its salt, and production thereof, said 2-cycloalkenylamine derivative being represented by the formula (I),

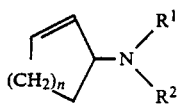

(I)

wherein $R^1$ represents a hydrogen atom, a hydroxyl, amino, lower cycloalkyl, lower cycloalkenyl, lower alkynyl, tetrahydrofurfuryl, piperidyl, arylthio, arylcarboxyl or aryl group, a lower alkyl group which may be substituted with a halogen atom or a cyano, nitro, hydroxyl, lower alkoxyl, lower cycloalkyl, aryl, carboxyl, lower alkoxycarbonyl, lower alkenyloxycarbonyl, aryloxycarbonyl, lower alkylcarbonyl or dialkylamino group, a lower alkenyl group which may be substituted with a halogen atom or an aryl group, or a lower alkoxyl group which may be substituted with an aryl group, $R^2$ represents a hydrogen atom, a hydroxyl, amino, lower cycloalkyl, lower cycloalkenyl, lower alkynyl, tetrahydrofurfuryl, piperidyl, arylthio, arylcarboxyl or aryl group, a lower alkyl group which may be substituted with a halogen atom or a cyano, nitro, hydroxyl, lower alkoxyl, lower cycloalkyl, aryl, carboxyl, lower alkoxycarbonyl, lower alkenyloxycarbonyl, aryloxycarbonyl, lower alkylcarbonyl or dialkylamino group, a lower alkenyl group which may be substituted with a halogen atom or an aryl group, a lower alkoxyl group which may be substituted with an aryl group, or a group represented by the formula,

wherein $R^3$ represents a hydrogen atom, a lower alkynyl, cycloalkyl, cycloalkenyl, aryl, lower alkyl-substituted oxathiinyl, uracilyl, arylcarbonyl or benzdioxanyl group, an alkyl group which may be substituted with a halogen atom or a lower alkoxyl, cycloalkoxyl, aryl, aryloxy, arylthio, cyano, carboxyl or lower alkoxycarbonyl group, or a lower alkenyl group which may be substituted with a halogen atom or a carboxyl lower alkoxyl or alkoxycarbonyl group, and X represents an oxygen or sulfur atom or an imino group, or $R^3$ and $R^1$, taken together, may form a lower alkylene or o-phenylene group, or $R^1$ and $R^2$, taken together, may form an alkylene or alkenylene group which may contain an oxygen or sulfur atom, a carbonyl group or an imino group or at least one of substituents, a group represented by the formula,

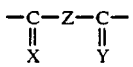

wherein X and Y, which may be the same or different, represent an oxygen or sulfur atom or an imino group, and Z represents a cycloalkylene, cycloalkenylene, bicycloalkylene or arylene group, a lower alkylene group which may be substituted with a hydroxyl, lower alkoxyl, aryl, lower alkylcarbonyloxy, methylene, alkylidene, mercapto, arylcarbamoyloxy which may be substituted, or lower alkylcarbonylthio group, a lower alkenylene group which may be substituted with a halogen atom or a carboxyl or aryl group, or a substituent represented by the formula —A—R— (in which A represents an oxygen or sulfur atom or an imino group, and R represents a lower alkylene group), or a substituted alkylidene group represented by the formula,

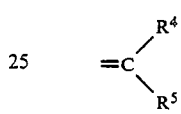

wherein $R^4$ and $R^5$, which may be the same or different, represent a hydrogen atom, a nitro, lower cycloalkyl, aryl, dihydropyranyl, carboxyl or acyl group, a lower alkyl group which may be substituted with a halogen atom or a hydroxyl, lower alkoxyl, aryloxy, lower alkoxycarbonyl, di-lower alkylamino, acyl or aryl group, a lower alkenyl group which may be substituted with a halogen atom or a hydroxyl or aryl group, or a lower alkynyl group which may be substituted with an aryl group, or $R^4$ and $R^5$, taken together, may form an alkylene or alkenylene group which may contain an oxygen or sulfur atom, a carbonyl group or an imino group, and n represents 1, 2, 3 or 4.

The present inventors made an extensive study on controlling agents for soil diseases, one of the plant diseases which are most difficult to control, and as a result, found that the present compound has excellent controlling effect on soil diseases caused by many plant pathogens.

In the plant pathogens on which the present compound has excellent controlling effect, there are included pathogens belonging to genus *Fusarium* such as *Fusarium oxysporum* f. sp. *licopersici* (fusarium wilt of tomato), *Fusarium oxysporum* f. sp. *raphani* (yellows of Japanese radish), *Fusarium oxysporum* f. sp. *cucumerinum* (fusarium wilt of cucumber), *Fusarium oxysporum* f. sp. *niveum* (fusarium wilt of watermelon), *Fusarium oxysporum* f. sp. *conglutinans* (yellows of cabbage), *Fusarium oxysporum* f. sp. *fragariae* (yellows of strawberry), *Fusarium nivale* f. sp. *graminicola* (fusarium snow blight of wheat), *Fusarium roseum* f. sp. *cerealis* (fusarium blight of wheat), *Fusarium solani* f. sp. *pisi* (root rot of pea) and *Fusarium oxysporum* f. sp. *vasinfectum* (fusarium wilt of cotton), pathogens belonging to genus Pythium such as *Pythium aphanidermatum* (damping-off of cucumber) and *Pythium debaryanum* (damping-off of tobacco), pathogens belonging to genus Rhizoctonia such as *Rhizoctonia solani* (damping-off of cucumber, black scurf of potato, root rot of sugar beet, rhizoctonia rot of zoysia grass, sore shin of tobacco), Rhizoctonia candida (damping-off of sugar beet) and Rhizoctonia bataticola (charcoal rot of soybean), pathogens belonging to genus Verticillium such as Verticillium alboatrum (verticillium wilt of eggplant and verticillium wilt of chinese cabbage) and Verticillium dahliae (verticillium wilt of udo), pathogens belonging to genus Corticium such as Corticium rolfsii (southern blight of kidney bean), pathogens belonging to genus Typhula such as Typhula incarnata and Typhula ishikariensis (typhula snow blight of wheat, typhula snow blight of alfalfa) and pathogens belonging to genus Plasmodiophora such as Plasmodiophora brassicae (clubroot of chinese cabbage, clubroot of cabbage), and the like.

The present compound, therefore, can be used as the active ingredient of soil disease-controlling agents for plowland, paddy field, orchard, tea garden, mulberry field, pasture, turf and the like.

In the foregoing formula (I) representing the present compound, the aryl group includes for example a phenyl, naphthyl, biphenyl, imidazolyl, triazolyl, pyrazolyl, thiazolyl, benzothiazolyl, triazinyl, pyrazinyl, pyrimidyl, uracilyl, furyl, pyridyl, quinolyl, pyrrolyl, quinoxalyl, benzimidazolyl, benzofuryl and thienyl groups, all of which may have a substituent. Specifically, there are given for example a phenyl, halogen-substituted phenyl, lower alkylphenyl, lower alkenylphenyl, lower haloalkylphenyl, nitrophenyl, cyanophenyl, carboxyphenyl, naphthyl, lower thioalkoxyphenyl, lower alkoxyphenyl, hydroxyphenyl, biphenyl, aryloxyphenyl, aryl-substituted alkoxyphenyl, formylphenyl, hydroxynaphthyl, nitronaphthyl, halobiphenyl, quinoxalyl, thienyl, lower alkylthienyl, lower alkoxycarbonylphenyl, benzoylphenyl, aryl-substituted lower alkoxyphenyl, di-lower alkylaminophenyl, lower acylaminophenyl, lower acylphenyl, imidazolyl, triazolyl, carbamoylphenyl, arylazophenyl, pyrazolyl, arylpyrazolyl, thiazolyl, benzothiazolyl, halothiazolyl, nitrothiazolyl, lower alkylthiazolyl, lower haloalkylthiazolyl, lower alkylbenzothiazolyl, arylthiazolyl, lower alkoxybenzothiazolyl, arylsulfonylthiazolyl, triazinyl, halotriazinyl, lower alkyltriazinyl, lower cycloalkenylaminotriazinyl, pyrazinyl, carboxypyrazinyl, pyrimidyl, halopyrimidyl, lower alkylpyrimidyl, halogenated lower alkylpyrimidyl, hydroxypyrimidyl, lower alkylthiopyrimidyl, uracilyl, furyl, benzofuryl, lower alkylbenzofuryl, lower alkylfuryl, lower haloalkylpyridyl, halopyridyl, lower alkylpyridyl, aryl lower alkoxypyridyl, hydroxypyridyl, nitropyridyl, pyridyl, lower alkylquinolyl, quinolyl, lower alkoxyquinolyl, pyrrolyl and N-lower alkylpyrrolyl groups, and the like.

In the foregoing formula (I) representing the present compound, the arylene group includes for example an o-phenylene and naphthylene groups and groups described below, all of which may be substituted with a halogen atom or a nitro or carboxyl group:

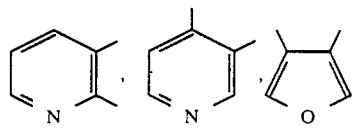

Next, a method for producing the present compound will be illustrated.

Method (a)

When the present compound is an amine compound represented by the formula (II),

wherein $R^6$ represents a hydrogen atom, a hydroxyl, amino, lower alkynyl, tetrahydrofurfuryl, piperidyl, arylthio, arylcarboxyl or aryl group, a lower alkyl group which is substituted with a halogen atom or a cyano, nitro, lower alkoxyl, carboxyl, lower alkoxycarbonyl, lower alkenyloxycarbonyl, aryloxycarbonyl, lower alkylcarbonyl or dialkylamino group, a lower alkenyl group which is substituted with a halogen atom or an aryl group, or a lower alkoxyl group which may be substituted with an aryl group, $R^8$ represents a lower alkynyl, tetrahydrofurfuryl, piperidyl, arylcarboxyl or arylthio group, a lower alkyl group which is substituted with a halogen atom or a cyano, nitro, lower alkoxyl, carboxyl, lower alkoxycarbonyl, lower alkenyloxycarbonyl, lower alkylcarbonyl, dialkylamino or aryloxycarbonyl group, a lower alkenyl group which is substituted with a halogen atom or an aryl group, or a lower alkoxyl group which may be substituted with an aryl group, and n represents the same meaning as above, it can be produced, for example, by reacting a compound represented by the formula (III),

wherein $R^6$ and n represent the same meanings as above, with the equivalent of a compound represented by the formula (IV),

wherein $R^8$ represents the same meaning as above, and L represents halogen atom, an arylcarboxyl, hydroxyl or lower alkylsulfonyloxy group, or a benzenesulfonyloxy group which may be substituted with a lower alkyl group, at 0° to 150° C. for 1 to 24 hours with or without a solvent in the presence or absence of the equivalent of an acid-binding agent.

As the compound represented by the formula (IV), there are given for example methyl iodide, ethyl iodide, 1-bromopropane, 2-bromopropane, 1-bromobutane, 1-bromo-2-methylpropane, 1-bromopentane, 1-bromo-3-methylbutane, 1-iodohexane, 1-bromoheptane, 2-bromo-5-ethylnonane, 3-bromopropionitrile, cyclopropylmethyl bromide, cyclohexyl bromide, 1-bromo-4-methylcyclohexane, cyclohexylmethyl bromide, 2,3,5-trimethylcyclohexylmethyl bromide, cyclopentyl bromide, tert-butyl bromide, cyclopropyl bromide, dibromomethane, diiodomethane, bromochloromethane, chlorodifluoromethane, bromotrichloromethane, tribromomethane, tetrabromomethane, 1-bromo-2-chloroethane, 1,2-dibromoethane, 1,1,1-trichloroethane, pentachloroethane, hexachloroethane, 1,1-dibromoethane, ethylene chlorohydrin, 2,2-dibromoethane, ethylene bromohydrin, 2,2-dichloroethanol, 2,2,2-trifluoroethanol, 1,2-dibromopropane, 1,3-dibromopropane, 1-bromo-3-chloropropane, 1,2,3-tribromopropane, 1,2-dibromobutane, 1,4-dibromobutane, 2,3-dibromobutane, 1-bromo-3-chloro-2-methylpropane, 1,5-dibromopentane, 1,6-dibromohexane, 1,3-dibromobutane, 2-iodo-1,1,1-trichloroethane, 1,1,2,2-tetrachloroethane, 1,1-dichloroethane, allyl bromide, 3-bromocycloheptene, 3-bromocyclooctene, 3-bromocyclohexene, 3-bromocyclopentene, propargyl bromide, methallyl chloride, 1-chloro-2-butene, 3-chloro-1-butene, 4-bromo-1-butene, 3-hexenyl bromide, 1,3-dichloro-1-propene, 2,3-dichloro-1-propene, 1,2,3-trichloropropene, 1,3-dichloro-2-butene, 1,4-dichloro-2-butene, cinnamyl chloride, bicyclo[2.2.1]-3-methylheptenylmethyl bromide, benzyl bromide, p-chlorobenzyl chloride, m-bromobenzyl bromide, o-fluorobenzyl bromide, 2,4-dichlorobenzyl chloride, p-methylbenzyl chloride, p-ethylbenzyl chloride, p-isopropylbenzyl chloride, p-tert-butylbenzyl bromide, vinylbenzyl chloride, 2,5-dimethylbenzyl chloride, m-trifluoromethylbenzyl chloride, m-nitrobenzyl bromide, m-cyanobenzyl bromide, α,α'-dichloro-p-xylene, αα'-dibromo-o-xylene, α-chloroethylbenzene, p-bromomethylbenzoic acid, phenethyl bromide, p-nitrophenethyl bromide, β-bromopropylbenzene, β-bromoisopropylbenzene, α,β-dibromoethylbenzene diphenylmethyl bromide, triphenylmethyl bromide, 2-chloro-4-nitrobenzyl chloride, 1-chloromethylnaphthalene, p-methoxybenzyl chloride, p-methylphenyl-n-butyl bromide, 2,4-dimethylphenethyl bromide, phenyl-n-butyl bromide, phenyl-n-propyl bromide, ethyl bromoacetate, methyl bromoacetate, isopropyl chloroacetate, n-butyl chloroacetate, phenyl chloroacetate, allyl chloroacetate, vinyl chloroacetate, methyl 2-chloropropionate, ethyl 2-bromopropionate, ethyl 2-bromopropionate, ethyl 2-bromobutyrate, ethyl 2-bromoisobutyrate, lactonitrile, hydroxyacetonitrile, acetone cyanhydrin, 2,6-dichloro-4-methylpyrimidine, 4-bromobutyronitrile, 5-bromovaleronitrile, 2-chloropropionitrile, chloroacetonitrile, bromoacetic acid, 2-chloropropionic acid, 2-bromo-n-butyric acid, α-bromoisobutyric acid, 2-bromoisovaleric acid, cyanuric chloride, 6-chloro-3-trifluoromethylpyridine, 5,6-dichloro-3-trifluoromethylpyridine, diethyl chlorosuccinate, 1,3-cyclohexanedione, phenylsulfenyl bromide, 2-methoxycarbonylphenylsulfenyl bromide, bromoacetone, benzoyl peroxide, 2-bromomethylbicyclo[2.2.1]heptane and the like.

Method (b)

When the present compound is an amine compound represented by the formula (V),

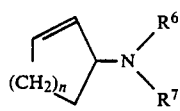

wherein $R^6$ and n represent the same meanings as above, and $R^7$ represents a hydrogen atom, a hydroxyl, amino, lower alkynyl, tetrahydrofurfuryl, piperidyl, arylthio or arylcarboxyl group, a lower alkyl group which is substituted with a halogen atom or a cyano, nitro, lower alkoxyl, carboxyl, lower alkoxycarbonyl, lower alkenyloxycarbonyl, aryloxycarbonyl, lower alkylcarbonyl or dialkylamino group, a lower alkenyl group which is substituted with a halogen atom or an aryl group, or a lower alkoxyl group which may be substituted with an aryl gruop, or $R^6$ and $R^7$, taken together, may form alkylene or alkenylene group which may contain an oxygen or sulfur atom, a carbonyl group, an imino group or at least one of substituents provided that a case wherein $R^6$ and $R^7$ are a hydrogen atom at the same time is excluded, it can be produced, for example, by reacting an amine represented by the formula (VI),

wherein $R^6$ and $R^7$ represent the same meanings as above, with 0.5 to 1 equivalent of a compound represented by the formula (VII),

wherein n represents the same meaning as above, and E represents a halogen atom, a lower alkylsulfonyloxy group or a benzenesulfonyloxy group which may be substituted with a lower alkyl group, with or without a solvent for 1 to 24 hours in the presence or absence of not less than the equivalent of an acid-binding agent.

As the compound represented by the formula (VI), there are given for example hydrazine, methylamine, ethylamine, n-propylamine, isopropylamine, n-amylamine, 2-ethylhexylamine, n-butylamine, isobutylamine, sec-butylamine, tert-butylamine, 2-methylallylamine, 3-cyclohexenylamine, allylamine, vinylamine, isoamylamine, neopentylamine, 1,2-dimethylpropylamine, n-hexylamine, n-heptylamine, 2-methylpentylamine, 1,3,3-tetramethylbutylamine, cyclopropylamine, cyclopentylamine, 3-methylcyclohexylamine, cyclohexylamine, 1,1-dimethylpropargylamine, 1,1-diethylpropargylamine, ethylpropargylamine, 2-chloroethylamine, 2-bromoethylamine, 3-bromopropylamine, 2,2,2-trifluoroethylamine, 2-methoxyethylamine, 2-ethoxyethylamine, aminoacetaldehyde dimethyl acetal, aminoacetaldehyde diethyl acetal, 3-methoxypropylamine, 3-ethoxypropylamine, 3-isopropoxypropylamine, butoxypropylamine, isobutoxypropylamine, 2-ethylhexyloxypropylamine, β-aminopropionitrile, cyclopropylmethylamine, cyclohexylmethylamine, N-(2-ethylhexyl)-2-cyclopentenylamine, dimethylamine, diethylamine, di-n-propylamine, di-(2-ethylhexyl)amine, N-methylcyclohexylamine, diallylamine, di n-butylamine, diisobutylamine, di-sec-butylamine, di-n-amylamine, diisoamylamine, di-n-hexylamine, dicyclohexylamine, N-methylpropargylamine, N-ethyl-n-butylamine, N-methyl-β-alanylnitrile β-aminoethanol, diisopropanolamine, isopropylcyclohexylamine, diisopropylamine, ethylbutylamine, N-(2-chloroethyl)methylamine, N-methylethanolamine, 2-ethylaminoethanol, 2-isopropylaminoethanol, 2-tert-butylaminoethanol, diethanolamine, N-(β-hydroxyethyl)-2-cyclopentenylamine, tris(oxymethyl)aminomethane, 1-hydroxyethylamine, 3-amino-1-propanol, 2-amino-1-propanol, 1-amino-2-propanol, 2-amino-1-butanol, diglycolamine, 5-amino-1-pentanol, 6-amino-1-hexanol, 3-amino-1,2-propanediol, 1-aminomethyl-1-cyclohexanol, N-phenylethanolamine, 2-benzylamino-1-propanol, N-n-butylethanolamine, 3-aminomethyl-3,5,5-trimethylcyclohexanol, benzylamine, 4-chlorobenzylamine, 4-methoxybenzylamine, 2,4-dichlorobenzylamine, N-methylbenzylamine, dibenzylamine, aminodiphenylmethane, α-methylbenzylamine, N-isopropylbenzylamine, 4-hydroxy-3-methoxybenzylamine, m-nitrobenzylamine, 2-methylbenzylamine, α-phenethylamine, phenethylamine, p-chlorophenethylamine, 4-bromophenylbutylamine, N-ethylbenzylamine, aniline, o-hydroxyaniline, o-nitroaniline, 3-nitro-4-aminotoluene, 2-chloro-4-nitroaniline, 4-methoxy-2-nitroaniline, 2-fluoro-5-nitroaniline, N-methyl-p-nitroaniline, p-n-butylaniline, o-phenylaniline, 3,4-dimethylaniline, 2,4,6-trimethylaniline, m-bromoaniline, o-fluoroaniline, 2,5-dichloroaniline, 3,5-dichloroaniline, 2,4,5-trichloroaniline, 2-chloro-6-methylaniline, 5-chloro-2-hydroxyaniline, 3-methoxy-6-chloroaniline, 3-trifluoromethyl-4-chloroaniline, 2-nitro-4-trifluoromethylaniline, 4-trifluoromethylaniline, 2-trifluoromethylaniline, 4-methoxy-3-trifluoromethylaniline, 2,4-dinitroaniline, 2-bromo-4,6-dinitroaniline. 3-cyano-4-chloroaniline, o-methoxyaniline, 4-methoxy-2-methylaniline, 2,5-dimethoxyaniline, 3,4,5-trimethoxyaniline, 3,4-dimethylenedioxyaniline, 6-amino-1,4-benzdioxane, p-phenoxyaniline, 2,4-dibenzyloxyaniline, 4-benzyloxyaniline, p-cresidine, N-ethylaniline, N-methoxy-o-toluidine, diphenylamine, N-methyl-p-nitroaniline, N-ethyl-o-toluidine N-methyl-p-anisidine, N-benzyl-p-anisidine, 8-amino-2-naphthol, 4-nitro-1-naphthylamine, 5,6,7,8-tetrahydro-1-naphthylamine, 1,2,3,4-tetrahydronaphthylamine, α-naphthylamine, 4-(2,4,6-trichlorophenyl)aniline, 4,4'-oxydianiline, 3-methylthioaniline, 4-aminobenzonitrile, ethyl m-aminobenzoate, p-aminoazobenzene, 2-aminobenzophenone, 4-aminobenzamide, m-aminoacetophenone, 1,2,4-triazole, 4-amino-1,2,4-triazole, 3-amino-2-phenylpyrazole, 3,5-dimethylpyrazole, 2-amino-thiazole, 2-aminobenzothiazole, 2-amino-5-chlorothiazole, 2-amino-5-nitrothiazole, 2-amino-4-methylthiazole, 2-amino-5,6-dihydro-4H-cyclopentathiazole, 2-amino-(4-chloromethyl)thiazole, 2-amino-5-(p-nitrophenylsulfonyl)thiazole, 2-amino-6-methoxybenzothiazole, 2-amino-6-methylbenzothiazole, 2-amino-4-phenylthiazole, benzimidazole, 2-benzimidazole methanol, 2-benzyl-2-imidazoline, 2-hydroxybenzimidazole, 2-methylthio-2-imidazoline, imidazole, 2-(1-naphthylmethyl)-2-imidazolin 2-ethylimidazole, 2-phenylimidazole, 4,5-dicyanoimidazole, 2,4,5-tribromoimidazole, 2-methyl-4,5-dicyanoimidazole, 4-nitroimidazole, 5-chlorobenzimidazole, 2-(α-hydroxybenzyl)benzimidazole, 3-amino-1,2,4-triazine, 3-amino-5,6-dimethyl-1,2,4-triazine, aminopyrazine, 3-aminopyrazine-2-carboxylic acid, 2-amino-4,6-dichloropyrimidine, 2-aminopyrimidine, 2-amino-4-chloro-6-hydroxypyrimidine, 4-amino-6-chloro-2-methylthiopyrimidine, 5-aminouracil, furfurylamine, tetrahydrofurfurylamine, hydroxylamine, N-methylhydroxylamine, O-methylhydroxylamine, O-ethylhydroxylamine, O,N-dimethylhydroxylamine, o-benzyloxyamine, 2-amino-5-bromopyridine, 6-amino-3-picoline, 2-amino-3-benzyloxypyridine, 2-amino-3-hydroxypyridine, 2-amino-5-nitropyridine, 2-aminopyridine, 2-aminomethylpyridine, 1,2,5,6-tetrahydropyridine, 8-amino-6-methylquinoline, 8-aminoquinoline, 3,5-diiodo-4-pyridone, 8-amino-6-methoxyquinoline, 1,2,3,4-tetrahydroquinoline, 1,2,3,4-tetrahydroisoquinoline, N-(3-aminopropyl)morpholine, 2,6-dimethylmorpholine, morpholine, thiomorpholine, 3-acetyl-2,4-dimethylpyrrole, 2,5-dimethylpyrrole, 2,5-dimethylpyrrolidine, pyrrole, pyrrolidine, 3-pyrroline, methyl pyrrole-2-carboxylate, 3-pyrrolidinol, N-methylpiperazine, 1-(o-methoxyphenyl)piperazine, 1-(2-pyridyl)piperazine, N-(α,α,α-trifluoromethyl-m-tolyl)piperazine, ethyleneimine, dodecamethyleneimine, hexamethyleneimine, 3-amino-N-ethylpiperidine, 4-amino-1-benzylpiperidine, N-(2-aminoethyl)piperidine 4-bromo-4-phenylpiperidine, 4-(p-chlorophenyl)-4-hydroxypiperidine, 4-cyano-4-phenylpiperidine, 2,6-dimethylpiperidine, piperidine, 2-piperidine ethanol, 2,2,6,6-tetramethyl-4-piperidone, 2,2,6,6-tetramethylpiperidine and the like.

The solvent used in the above methods (a) and (b) includes for example aliphatic hydrocarbons such as hexane, heptane, ligroin, petroleum ether, etc., aromatic hydrocarbons such as benzene, toluene, xylene, etc., halogenated hydrocarbons such as chloroform, carbon tetrachloride, dichloroethane, chlorobenzene, dichlorobenzene, etc., ethers such as diethyl ether, diisopropyl ether, dioxane, tetrahydrofuran, diethylene glycol dimethyl ether, etc., nitro compounds such as nitroethane, nitrobenzene, etc., nitriles such as acetonitrile, isobutyronitrile, etc., tertiary amines such as pyridine, triethylamine N,N-diethylaniline, tributylamine, N-methylmorpholine, etc., acid amide such as N,N-dimethylformamide, acetamide, etc., sulfur compounds such as dimethyl sulfoxide, sulfolane, etc., and mixtures thereof.

Also, the acid-binding agent includes for example organic bases such as pyridine, triethylamine, N,N-diethylaniline, etc., and inorganic bases such as sodium carbonate, potassium carbonate sodium hydride, etc.

After completion of the reaction, the reaction solution is after-treated as usual, for example it is poured into water and the organic layer is separated and concentrated. If necessary, the product obtained is purified by chromatography, distillation, recrystallization and the like.

Next, examples of production of the present compound by the methods (a) and (b) will be shown.

PRODUCTION EXAMPLE 1

To a mixture of 2-cyclohexenylamine (0.97 g, 10 mmoles), triethylamine (1.01 g, 10 mmoles) and chloroform (10 ml) was added dropwise ethyl bromoacetate (1.67 g, 10 mmoles) at 0° to 5° C. After completion of the addition, the resulting mixture was heated under reflux for 3 hours.

Then the reaction solution was after-treated as usual and purified by chromatography to obtain 1.28 g of N-(2-cyclohexenyl)glycine ethyl ester [Compound (1)].
$n_D^{23.3}$ 1.4711

PRODUCTION EXAMPLE 2

2-Cycloheptenylamine (1.11 g, 10 mmoles) was added dropwise to a mixture of an aqueous 50 wt. % hydroxyacetonitrile solution (1.14 g, 10 mmoles) and an aqueous 50% EtOH (10 ml) at 35° to 40° C.

After the resulting mixture was kept at this temperature for 30 minutes, it was after-treated as usual and purified by chromatography to obtain 1.35 g of N-(2-cycloheptenyl)glycinonitrile [Compound (2)].
$n_D^{24.0}$ 1.4950

PRODUCTION EXAMPLE 3

A mixture of 3-bromocycloheptene (1.75 g, 10 mmoles), triethylamine (1.01 g, 10 mmoles), morpholine (0.87 g, 10 mmoles) and chloroform (10 ml) was heated under reflux for 3 hours. After completion of the refluxing, the reaction mixture was after-treated as usual and purified by chromatography to obtain 0.91 g of N-(2-cycloheptenyl)morpholine [Compound (3)].

$n_D^{25.2}$ 1.5039

Some of the present compounds which can be produced by these methods are shown in Table 1.

TABLE 1

Present compounds represented by the formula,

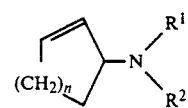

| Compound No. | $R^1$ | $R^2$ | n | Physical constant |
|---|---|---|---|---|
| (1) | H | —CH$_2$COOC$_2$H$_5$ | 2 | $n_D^{23.3}$ 1.4711 |
| (2) | H | —CH$_2$CN | 3 | $n_D^{24.0}$ 1.4950 |
| (3) | —CH$_2$CH$_2$OCH$_2$CH$_2$— | | 3 | $n_D^{25.2}$ 1.5039 |
| (4) | H | —C(CH$_3$)$_2$CN | 3 | $n_D^{26.2}$ 1.4791 |
| (5) | H | —CH(CH$_3$)CN | 3 | $n_D^{26.0}$ 1.4813 |
| (6) | H | —CH$_2$COOCH$_3$ | 3 | $n_D^{22.2}$ 1.4811 |
| (7) | H | —CH$_2$COOC$_2$H$_5$ | 3 | $n_D^{22.9}$ 1.4761 |
| (8) | H | cycloheptenyl | 3 | $n_D^{22.0}$ 1.5202 |
| (9) | H | 3-nitropyridin-2-yl | 3 | m.p. 105° C. |
| (10) | H | cyclopropyl | 3 | $n_D^{25.5}$ 1.4986 |
| (11) | H | cyclohexyl | 2 | $n_D^{18.8}$ 1.5128 |
| (12) | H | —OCH$_3$ | 2 | $n_D^{30.2}$ 1.4680 |
| (13) | H | 2,4-dichlorophenyl | 3 | $n_D^{26.7}$ 1.5784 |
| (14) | H | —CH$_2$-(2-fluorophenyl) | 3 | $n_D^{26.6}$ 1.5280 |
| (15) | H | —CH$_2$C≡CH | 3 | $n_D^{23.7}$ 1.5030 |
| (16) | H | 4-(trifluoromethyl)phenyl | 3 | $n_D^{22.7}$ 1.5196 |
| (17) | H | —CH(CH$_3$)$_2$ | 3 | $n_D^{24.8}$ 1.4702 |
| (18) | H | —CH$_2$COCH$_3$ | 3 | $n_D^{17.2}$ 1.5375 |
| (19) | H | —(CH$_2$)$_5$Cl | 3 | $n_D^{23.5}$ 1.4990 |
| (20) | —CBr=NCBr=CBr— | | 2 | $n_D^{24.0}$ 1.6041 |

TABLE 1-continued

Present compounds represented by the formula,

| Compound No. | $R^1$ | $R^2$ | n | Physical constant |
|---|---|---|---|---|
| (21) | —N=CCH$_3$—CH=CCH$_3$— | | 3 | $n_D^{23.9}$ 1.5189 |
| (22) | H | —CH$_2$COOH | 3 | m.p. >300° C. (dec.) |
| (23) | H | —CHCH$_3$COOCH$_3$ | 3 | $n_D^{22.3}$ 1.4718 |
| (24) | H | —CH$_2$CN | 2 | $n_D^{20.1}$ 1.5231 |
| (25) | H | —C$_2$H$_5$ | 2 | $n_D^{21.6}$ 1.4781 |
| (26) | H | —OCH$_2$-phenyl | 2 | $n_D^{29.7}$ 1.5330 |
| (27) | H | —CHCOOC$_2$H$_5$ / CH$_2$COOC$_2$H$_5$ | 2 | $n_D^{30.1}$ 1.4640 |
| (28) | H | —OC$_2$H$_5$ | 2 | $n_D^{30.1}$ 1.4629 |
| (29) | H | 3-oxocyclohex-1-en-1-yl | 2 | Resinous product |
| (30) | H | 3-(trifluoromethyl)pyridin-2-yl | 2 | m.p. 82–84° C. |
| (31) | H | 4-chloro-3-(trifluoromethyl)pyridin-2-yl | 2 | $n_D^{29.5}$ 1.5170 |
| (32) | H | 3-nitropyridin-2-yl | 2 | m.p. 108–110° C. |
| (33) | —CH=N—CH=CH— | | 2 | $n_D^{30.4}$ 1.5165 |
| (34) | —CH=N—CH=N— | | 2 | $n_D^{26.4}$ 1.5142 |
| (35) | H | 2-methyl-3-nitrothiophen-...-yl | 2 | m.p. 144° C. |
| (36) | H | —S-phenyl | 2 | Resinous product |
| (37) | H | —NH$_2$ | 2 | $n_D^{30.0}$ 1.4778 |

TABLE 1-continued

Present compounds represented by the formula,

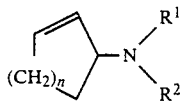

| Compound No. | R¹ | R² | n | Physical constant |
|---|---|---|---|---|
| (38) | H | (dichloro-triazinyl with dimethyl group) | 2 | m.p. >300° C. |
| (39) | H | (chloro-triazinyl with cyclohexenylamino and dimethyl) | 2 | m.p. 153–155° C. |
| (40) | H | —S—C₆H₄—COCH₃ | 2 | $n_D^{24.7}$ 1.5930 |
| (41) | H | —OC(O)—C₆H₅ | 2 | $n_D^{24.2}$ 1.5495 |
| (42) | H | —CH₂COOCH₃ | 2 | $n_D^{18.5}$ 1.4791 |
| (43) | H | —CH(CH₃)COOCH₃ | 2 | $n_D^{20.7}$ 1.4694 |
| (44) | H | —CH₂COOH | 2 | m.p. 208° C. |
| (45) | H | —CH₂—C₆H₄—Cl | 2 | $n_D^{17.5}$ 1.5550 |
| (46) | H | —CHCH₃CN | 2 | $n_D^{17.3}$ 1.4855 |
| (47) | H | —C(CH₃)₂CN | 2 | $n_D^{17.3}$ 1.4796 |
| (48) | H | —CH₂CN | 1 | $n_D^{25.0}$ 1.4819 |
| (49) | H | —CH₂CN | 4 | $n_D^{24.7}$ 1.4921 |
| (50) | H | —C₆H₅ | 3 | $n_D^{25.2}$ 1.5930 |

Method (c)

When the present compound is an acid amide compound represented by the formula (VIII),

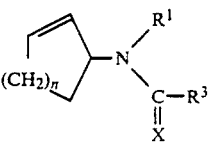

wherein R³, X and n represent the same meanings as above, provided that when X is an oxygen atom and R¹ is a hydrogen atom, the following combinations of n and R³ are excluded: n=1 and R³=methyl or phenyl; n=2 and R³=methyl, propyl, phenyl, chloromethyl, trichloromethyl, tert-butyl or trifluoromethyl; n=3 and R³=methyl or trifluoromethyl; n=4 and R³=methyl, when X is an oxygen atom, R¹ is benzyl and n is 1, R³ is not methyl, and when X is an imino group, R¹ is a hydrogen atom and n is 2, R³ is not a trichloromethyl group, it can be produced, for example, by reacting a compound represented by the formula (IX),

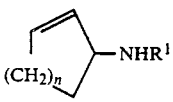

wherein R¹ and n represent the same meanings as above, with 1.0 to 1.1 equivalent of a compound represented by the formula (X),

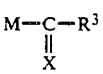

wherein R³ and X represent the same meanings as above, and M represents a halogen atom, a hydroxyl, lower alkoxyl, mercapto or lower alkylthio group, or a group represented by the formula

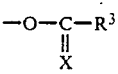

(in which R³ and X represent the same meanings as above), at −78° to 200° C. for several minutes to 24 hours in a solvent in the presence or absence of 1.0 to 1.1 equivalent of an acid-binding agent, or by simply heating the both compounds at high temperatures and removing the formed hydrogen chloride, water, lower alcohol, hydrogen sulfide or lower mercaptan.

As the above compound represented by the formula (X), there are given for example formic acid, ethyl formate, acetic acid, acetyl chloride, propionic acid, propionyl chloride, 2-methylpropionic acid, 2-methylpropionyl chloride, 2,2-dimethylpropionic acid, 2,2-dimethylpropionyl chloride, 3,3-dimethylbutanoic acid, 3,3-dimethylbutanoyl chloride, myristic acid, 2,2,3,3,3-pentafluoropropionic acid, 2,2,3,3,3-pentafluoropropionyl chloride, chloroacetyl chloride, trichloroacetyl chloride, chloroacetic acid, trichloroacetic acid, dichloroacetic acid, dichloroacetyl chloride, methoxyacetyl chloride, methoxyacetic acid, l-menthoxyacetic acid, l-menthoxyacetyl chloride, cyanoacetic acid, cyanoacetyl chloride, methyl cyanoacetate, ethyl cyanoacetate, phenoxyacetic acid, phenoxyacetyl chloride, phenylthioacetic acid, phenylthioacetyl chloride, phenylacetic acid, phenylacetyl chloride, o-, m- or p-chlorophenylacetic acid, o-, m- or p-chlorophenylacetyl chloride, α-chlorophenylacetic acid, α-chlorophenylacetyl chloride, crotonic acid, crotonyl chloride, 2-phenylpropionic acid, 2-phenylpropionyl chloride, o-, m- or p-tolylacetic acid, o-, m- or p-tolylacetyl chloride, 3-chloropropenoic acid, 3-chloropropenoyl chloride, propargylic acid, methyl propargylate, ethyl propargylate, 2-butynoic acid, ethyl 2-butynoate, 3-butynoic acid, 3-butynoyl chloride, methyl 3-butynoate, ethyl 3-butynoate, cyclohexanecarboxylic acid, cyclohexanecarbonyl chloride, cyclobutanecarboxylic acid, cyclobutanecarbonyl chloride, cyclopropanecarboxylic acid, cyclopropanecarbonyl chloride, 3-cyclohexenecarboxylic acid, 3-cyclohexenecarbonyl chloride, benzoic acid, benzoyl chloride, o-, m- or p-chlorobenzoic acid, o-, m- or p-chlorobenzoyl chloride, o-, m- or p-methylbenzoic acid, o-, m- or p-methylbenzoyl chloride, salicylic acid, o-, m- or p-methoxybenzoic acid, o-, m- or p-methoxybenzoyl chloride, 2,6-dimethylbenzoic acid, 2,6-dimethylbenzoyl chloride, 2,4-dichlorobenzoic acid, 2,4-dichlorobenzoyl chloride, o- or m-trifluoromethylbenzoyl chloride, o- or m-trifluoromethylbenzoic acid, p-fluorobenzoic acid, p-fluorobenzoyl chloride, 4-tert-butylthiobenzoic acid, O-ethyl 4-tert-butylthiobenzoate, ethyl 4-tert-butyldithiobenzoate, 1-naphthoic acid, 1-naphthoyl chloride, 2- or 3-furoic acid, 2- or 3-furoyl chloride, 2,5-dimethyl-3-furoic acid, 2,5-dimethyl-3-furoyl chloride, 3-methyl-2-furoic acid, 3-methyl-2-furoyl chloride, isonicotinic acid, isonicotinyl chloride, N-methylpyrrole-2-carboxylic acid, N-methylpyrrole-2-carbonyl chloride, 2-quinoxalinecarbonyl chloride, 2-quinoxalinecarboxylic acid, 2-thiophenecarboxylic acid, 2-thiophenecarbonyl chloride 2-benzimidazolecarboxylic acid, 3-methyl-5-isoxazolecarboxylic acid, 3-methylisoxazolecarbonyl chloride, 2,4-dimethyl-4-oxazolinecarboxylic acid, 2,4-dimethyl-4-oxazolinecarbonyl chloride, 2-pyrazinecarboxylic acid, 2-pyrazinecarbonyl chloride, 2,4-dihydroxypyrimidine-5-carboxylic acid, 1,2,4-triazole-5-carboxylic acid, 1,4-benzdioxane-2-carboxylic acid, 1,4-benzdioxane-2-carbonyl chloride, 4-pyrazolecarboxylic acid, 5-imidazolecarboxylic acid, 2,3-dihydro-6-methyl-5-oxathiinecarboxylic acid, 2,3-dihydro-6-methyl-5-oxathiinecarbonyl chloride, succinic acid, maleic acid, phthalic acid, itaconic acid, monomethyl succinate, monoethyl maleate, monoethyl phthalate, monoethyl itaconate, tetrachlorophthalic acid, dimethylmaleic acid, monoethyl tetrachlorophthalate, monoethyl 2,2-dimethylglutarate, glutaric acid, 2,2-dimethylglutaric acid, monoethyl glutarate, monoethyl 2,2-dimethylglutarate, 3,3-dimethylglutaric acid, citraconic acid, monoethyl 3,3-dimethylglutarate, monoethyl citraconate, tetrabromophthalic acid, monoethyl tetrabromophthalate, dithioacetic acid, trifluorodithioacetic acid, dithiobenzoic acid, O-ethyl thioacetate, O-methyl thiobenzoate, O-methyl p-methoxythiobenzoate, thioacetyl chloride, ethyl dithioacetate methyl dithioisovalerate, methyl p-chlorodithiobenzoate, methyl p-hydroxydithiobenzoate, o-iodobenzoic acid, o-iodobenzoyl chloride, imidazolylacetic acid, triazolylacetic acid, 3,5-bis(trifluoromethyl)benzoic acid, 3,5-bis(trifluoromethyl)benzoyl chloride, 5-chloropentanoyl chloride, diphenylacetyl chloride, 4-chloro-2-methylphenoxyacetic acid, benzoylformyl chloride, 1,4-benzdioxane-6-acetyl chloride, 3-chloropropionyl chloride, butanoyl chloride, 3-methylbutanoyl chloride bromoacetyl bromide, isobutoxyacetyl chloride, propenoyl chloride, 3-ethoxypropenoyl chloride, cinnamoyl chloride, 2-fluorocinnamoyl chloride, m-nitrobenzoyl chloride, 2-phenylcyclopropanecarbonyl chloride, 1-methylcyclopropanecarbonyl chloride, 2,2,3,3-tetramethylcyclopropanecarbonyl chloride, m-bromobenzoyl chloride, m-cyanobenzoyl chloride, p-dimethylaminobenzoyl chloride, m-fluorobenzoyl chloride, 2-chloro-4-nitrobenzoyl chloride, m-fluorobenzoic acid, 2-nitro-3-phenoxybenzoyl chloride, 2,2-dimethyl-3-(2,2-dichloroethenyl)cyclopropanecarboxylic acid chloride, nicotinic acid, 3,5-dichlorobenzoyl chloride, nicotinyl chloride, pyrrole-2-carbonyl chloride, propyl 3-chloroformyl-3-butenoate, pyrrole-2-carboxylic acid, 3-methylbenzofuran-2-carboxylic acid chloride, chloroacetimidoyl chloride, methyl 3-chloroformylpropanoate, trichloroacetimidic acid and the like.

Also, as an acid anhydride among the compounds represented by the formula (X), there are given for example anhydrides of the following compounds: Acetic acid, propionic acid, 2-methylpropionic acid, 2,2-dimethylpropionic acid, 3,3-dimethylbutanoic acid, myristic acid, 2,2,3,3-pentafluoropropionic acid, chloroacetic acid, dichloroacetic acid, trichloroacetic acid, methoxyacetic acid, l-menthoxyacetic acid, cyanoacetic acid, phenoxyacetic acid, phenylthioacetic acid, phenylacetic acid, o-, m- or p-chlorophenylacetic acid, α-chlorophenylacetic acid, crotonic acid, 2-phenylpropionic acid, o-, m- or p-tolylacetic acid, 3-chloropropenoic acid, propargylic acid, 2-butynoic acid, 3-butynoic acid, cyclohexanecarboxylic acid, cyclobutanecarboxylic acid, cyclopropanecarboxylic acid, 3-cyclohexenecarboxylic acid, benzoic acid, o-, m- or p-chlorobenzoic acid, o-, m- or p-methylbenzoic acid, salicylic acid, o-, m- or p-methoxybenzoic acid, 2,6-dimethylbenzoic acid, 2,4-dichlorobenzoic acid, o- or m-trifluoromethylbenzoic acid, p-fluorobenzoic acid, 1-naphthoic acid, 2- or 3-furoic acid, 2,5-dimethyl-3-furoic acid, 3-methyl-2-furoyl chloride, isonicotinic acid, N-methylpyrrole-2-carboxylic acid, 2-quinoxalinecarboxylic acid, 2-thiophenecarboxylic acid, 2-benzimidazolecarboxylic acid, 3-methyl-5-isoxazolecarboxylic acid, 2,4-dimethyl-4-oxazolinecarboxylic acid, 2-pyrazinecarboxylic acid, 2,4-dihydroxypyrimidine-5-carboxylic acid, 1,2,4-triazole-5-carboxylic acid, 1,4-benzdioxane-2-carboxylic acid, 4-pyrazolecarboxylic acid, 5-imidazolecarboxylic acid, 2,3-dihydro-6-methyl-5-oxathiinecarboxylic acid, n-butyric acid, n-valeric acid, isovaleric acid, lauric acid, caproic acid, trifluoroacetic acid and the like.

Method (d)

When the present compound is an acid amide compound represented by the formula (XI),

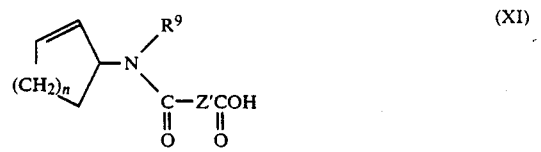

wherein $R^9$ represents a hydrogen atom, a hydroxyl, lower cycloalkyl, lower cycloalkenyl, lower alkynyl, tetrahydrofurfuryl, piperidyl, arylthio, arylcarboxyl or aryl group, a lower alkyl group which may be substituted with a halogen atom or a cyano, hydroxyl, lower alkoxyl, lower cycloalkyl, aryl, carboxyl, lower alkoxycarbonyl, lower alkenyloxycarbonyl, aryloxycarbonyl, lower alkylcarbonyl or dialkylamino group, a lower alkenyl group which may be substituted with a halogen atom or an aryl group, or a lower alkoxyl group which may be substituted with an aryl group, Z' represents a cycloalkenylene, cycloalkylene, bicycloalkylene or arylene group, a lower alkylene group which may be substituted with a hydroxyl, lower alkoxyl, aryl, lower alkylcarbonyloxy, methylene, alkylidene, mercapto, carbamoyloxy group which may be substituted, or lower alkylcarbonylthio group, or a lower alkenylene group which may be substituted with a halogen atom or a carboxyl or aryl group, and n represents the same meaning as above, it can be produced, for example, by reacting a compound represented by the formula (XII),

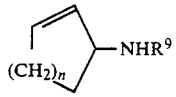  (XII)

wherein $R^9$ and n represent the same meanings as above, with 1.0 to 1.1 equivalent of a compound represented by the formula (XIII),

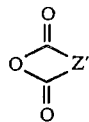  (XIII)

wherein Z' represents the same meaning as above, at −78° to 200° C. for 1 to 24 hours with or without a solvent.

As the compound represented by the formula (XIII, there are given for example the anhydrides of succinic acid, maleic acid, phthalic acid, itaconic acid, tetrachlorophthalic acid, dimethylmaleic acid, glutaric acid, 2,2-dimethylglutaric acid, 3,3-dimethylglutaric acid, citraconic acid, tetrabromophthalic acid, 1,2-cyclohexanedicarboxylic acid, isopropylidenesuccinic acid, 3,4,5,6-tetrahydrophthalic acid, mellitic acid, 4-carboxyphthalic acid, dichloromaleic acid, phenylmaleic acid, 3-nitrophthalic acid, 1,2-pyridinedicarboxylic acid, 3,4-furandicarboxylic acid, 3,4-pyrazinedicarboxylic acid, naphthalic acid, 1,2-cyclobutanedicarboxylic acid, monochloromaleic acid, monobromomaleic acid, debromomaleic acid, monofluoromaleic acid, difluoromaleic acid, malic acid, thiomalic acid, methoxysuccinic acid, 2-methyl-2-phenylsuccinic acid, acetoxysuccinic acid, acetylthiosuccinic acid, tetrafluorophthalic acid, 5-norbornane-2,3-dicarboxylic acid, 1,2-dimethyl-1,2-cyclopropanedicarboxylic acid, camphanic acid, diphenic acid, diphenylcarbamoyloxysuccinic acid, cis, cis, cis, cis-1,2,3,4-cyclopentanetetracarboxylic acid and the like.

Method (e)

When the present compound is an acid amide compound represented by the formula (XIV),

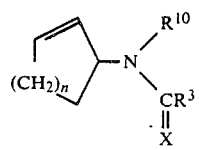  (XIV)

wherein $R^{10}$ represents a lower cycloalkyl, lower cycloalkenyl, arylthio, lower alkynyl, tetrahydrofurfuryl, piperidyl, arylcarboxyl or aryl group, a lower alkyl group which may be substituted with a halogen atom or a cyano, hydroxyl, lower cycloalkyl, aryl, carboxyl, lower alkoxycarbonyl, lower alkenyloxycarbonyl, aryloxycarbonyl, lower alkylcarbonyl or dialkylamino group, or a lower alkenyl group which may be substituted with a halogen atom or an aryl group, and $R^3$ and n represent the same meanings as above, it can be produced by reacting a compound represented by the formula (XV),

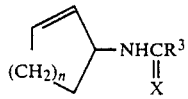  (XV)

wherein $R^3$, X and n represent the same meanings as above, with not less than the equivalent of a compound represented by the formula (XVI), $R^{10}$—L'  (XVI)

wherein $R^{10}$ represents the same meaning as above, and L' represents a halogen atom, an arylcarboxyl or lower alkylsulfonyloxy group, or a benzenesulfonyloxy group which may be substituted with a lower alkyl group, with or without a solvent at 0° to 150° C. for 1 to 24 hours in the presence of not less than the equivalent of an acid-binding agent.

Method (f)

When the present compound is represented by the foregoing formula (VIII) (provided that when X is an oxygen atom and $R^1$ is a hydrogen atom, the following combinations of n and $R^3$ are excluded: n=1 and $R^3$=methyl or phenyl; n=2 and $R^3$=methyl, propyl, phenyl, chloromethyl, trichloromethyl, tert-butyl or trifluoromethyl; n=3 and $R^3$=methyl or trifluoromethyl; n=4 and $R^3$=methyl, when X is an oxygen atom, $R^1$ is benzyl and n is 1, $R^3$ is not methyl, and when X is an imino group, $R^1$ is a hydrogen atom and n is 2, $R^3$ is not a trichloromethyl group), it can also be produced, for example, by reacting a compound represented by the formula (XVII),

  (XVII)

wherein $R^1$, $R^3$ and X represent the same meanings as above, with not less than the equivalent of a compound represented by the foregoing formula (VII) with or without a solvent at 0° to 150° C. for 1 to 24 hours in the presence of not less than the equivalent of an acid-binding agent.

As the compound represented by the formula (XVII), there are given for example formamide, pentan amide, butan amide, N-ethylacetamide, acetamide, chloroacetamide, dichloroacetamide, trichloroacetamide, N-tert-butylacetamide, malonamide, N-methylchloroacetamide, cyanoacetamide, N-(2-hydroxyethyl)acetamide, methacrylamide, lactamide, 2,2-dimethylpropan amide, N-methylformamide, trifluoroacetamide, N-ethylformamide, octadecan amide, N-(hydroxymethyl)acrylamide, thioacetamide, propan amide, N-(2-chloroethyl)acetamide, N-methylacetamide, 2-hydroxybenzanilide, acetanilide, 2'-hydroxyacetamide, nicotinamide, formanilide, thioisonicotinamide, ω-thiocaprolactam, benzanilide, 5-chloro-2-hydroxybenzanilide, 3'-nitroacetanilide, 4'-chloroacetanilide, 3'-chloroacetanilide, 4-hydroxybenzamide, 3,5-dinitrobenzamide, 3-nitrobenzamide, benzhydroxamic acid. 2',5'-dichloroacetanilide, 2-cyanobenzamide, acetylacetanilide, 2'-methylacetanilide, 2,6-dichlorobenzamide, 2'-chloroacetylacetanilide, 2'-methylacetylacetanilide, phenylacetamide, pyrazine-2-carboxamide, N-methyl-2-methylbenzamide, N-methylbenzamide, 3,4,5-trimethoxybenzamide, 3-chloroacetanilide, 4'-chloroacetylacetanilide, 4-nitrobenzamide, 2-cyanoacetanilide, 2-chlorobenzamide, 2-nitrobenzamide, 3'-hydroxyacetanilide 3'-methylacetanilide, 3-chlorobenzamide, 4'-hydroxyacetanilide, 2'-hydroxyacetanilide, 2-pyrrolidone, 1,2-benzisothiazol-3(2H)-one and the like.

Method (g)

When the present compound is an acid amide compound represented by the formula (XVIII),

(XVIII)

wherein R$^1$, R$^3$ and n represent the same meanings as above, it can be produced, for example, by reacting a compound represented by the formula (XIX),

(XIX)

wherein R$^1$, R$^3$ and n represent the same meanings as above, with not less than the equivalent of phosphorus pentasulfide at 25° to 150° C. for 1 to 24 hours in the presence or absence of a solvent.

The solvent used in the foregoing methods (c) to (g) includes for example aliphatic hydrocarbons such as hexane, heptane, ligroin, petroleum ether, etc., aromatic hydrocarbons such as benzene, toluene, xylene, etc., halogenated hydrocarbons such as chloroform, carbon tetrachloride, dichloroethane, chlorobenzene, dichlorobenzene, etc., ethers such as diethyl ether, diisopropyl ether, dioxane, tetrahydrofuran, diethylene glycol dimethyl ether, etc., ketones such as acetone, methyl ethyl ketone, methyl isobutyl ketone, isophorone, cyclohexanone, etc., esters such as ethyl formate, ethyl acetate, butyl acetate, diethyl carbonate, etc., nitro compounds such as nitroethane, nitrobenzene, etc., nitriles such as acetonitrile, isobutyronitrile, etc., tertiary amines such as pyridine, triethylamine, N,N-diethylaniline, tributylamine, N-methylmorpholine, etc., acid amides such as formamide, N,N-dimethylformamide, acetamide, etc., sulfur compounds such as dimethyl sulfoxide, sulfolane, etc., and mixtures thereof. Also, the acid-binding agent includes for example organic bases such as pyridine, triethylamine, N,N-diethylaniline, etc., and inorganic bases such as sodium carbonate, potassium carbonate, sodium hydroxide, etc. After completion of the reaction, the reaction solution is after-treated as usual, and if necessary, the product obtained is purified by chromatography, distillation, recrystallization and the like.

Next, examples of production of the present compound by the methods (c) to (g) will be shown.

PRODUCTION EXAMPLE 4

To a mixture of 2-cycloheptenylamine (1.11 g, 10 mmoles), triethylamine (1.01 g, 10 mmoles) and chloroform (10 ml), propionyl chloride (0.93 g, 10 mmoles) was added dropwise at 0° to 5° C. After stirring at 20° C. for 3 hours, the reaction mixture was poured into a 1N hydrochloric acid, and the separated organic layer was washed with a saturated aqueous sodium chloride solution and concentrated to obtain 1.50 g of N-(2-cycloheptenyl)propionamide [Compound (51)].
m.p. 84° C.

PRODUCTION EXAMPLE 5

To a chloroform (50 ml) solution of succinic anhydride (1.00 g, 10 mmoles), 2-cycloheptenylamine (1.11 g, 10 mmoles) was added dropwise at 0° to 5° C. After stirring at 61° C. for 5 hours, the reaction mixture was cooled to obtain a crystal. The crystal was recrystallized from an ethyl acetate/hexane mixture ot obtain 1.67 g of N-(2-cycloheptenyl)-1,4-butanedicarboxylic acid monoamide [Compound (52)].
m.p. 132°–133° C.

PRODUCTION EXAMPLE 6

To a dichloromethane solution (13 ml) containing salicyclic acid (1.38 g, 10 mmoles), dicyclohexylcarbodiimide (2.06 g, 10 mmoles) was slowly added at 0° C. After this mixture was stirred for 15 minutes, and 2-cyclohexenylamine (0.97 g, 10 mmoles) was added dropwise. The mixture was then heated to room temperatuer and stirred for 5 hours. The formed crystal was filtered off, the floating solid was removed by filtration and 13 ml of cold water was added to the filtrate. The organic layer was separated and washed with 3M hydrochloric acid, a saturated aqueous sodium hydrogencarbonate solution and a saturated aqueous sodium chloride solution in this order. After drying the organic layer over magnesium sulfate, the solvent was removed and the residual oil was purified by column chromatography on silica gel [ethyl acetate:hexane=3:1 (v/v)] to obtain 1.78 g of N-(2-cyclohexenyl)salicylic acid amide [Compound (53)].
$n_D^{22.4}$ 1.5781

PRODUCTION EXAMPLE 7

To a suspension (10 ml) of sodium hydride (0.24 g, 10 mmoles) in dimethylformamide was added dropwise at 0° C. a dimethylformamide solution (1 ml) of N-methylbenzamide (1.35 g, 10 mmoles). After completion of the addition, the temperature was raised to room temperature, and after stirring for 15 minutes, 3-bromocycloheptene (1.75 g, 10 mmoles) was added dropwise. The resulting mixture was stirred at room temperature for 24 hours, poured into water (20 ml) and extracted with ether. The oily product obtained by concentration was purified by chromatography on silica gel to obtain 0.92 g of N-methyl-N-(2-cycloheptenyl)benzamide [Compound (54)].
$n_D^{26.1}$ 1.5467

PRODUCTION EXAMPLE 8

To a suspension (10 ml) of sodium hydride (0.24 g, 10 mmoles) in DMF was added N-(2-cycloheptenyl)acetamide (1.53 g, 10 mmoles) in DMF (1 ml) at 0° C. After completion of the addition, the temperature of the mixture was raised to room temperature, and after stirring for 15 minutes, methyl iodide (2.84 g, 20 mmoles) was added dropwise. The resulting mixture was stirred at room temperature for 24 hours, poured into water (20 ml) and extracted with ether. The oily product obtained by concentration was purified by chromatography on silica gel to obtain 0.84 g of N-methyl-N-(2-cycloheptenyl)acetamide [Compound (55)].

$n_D^{24.5}$ 1.4968

PRODUCTION EXAMPLE 9

A mixture of N-(2-cyclohexenyl)-4-tert-butylbenzamide (3.78 g, 14.7 mmoles), phosphorus pentasulfide (1.65 g) and pyridine (17.6 ml) was heated under reflux for 3 hours. Thereafter, the reaction mixture was cooled, poured into water and extracted with ether. The organic layer was dried over anhydrous magnesium sulfate and concentrated. The oily product obtained was purified by column chromatography on silica gel to obtain 0.71 g of the objective compound [Compound (205)], m.p. 88°–91° C.

Some of the present compounds which can be produced by these methods are shown in Table 2.

TABLE 2

Present compounds represented by the formula

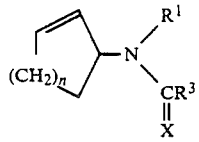

| Compound No. | $R^1$ | $R^3$ | n | X | Physical constant |
|---|---|---|---|---|---|
| (51) | H | —CH$_2$CH$_3$ | 3 | O | m.p. 84° C. |
| (52) | H | —CH$_2$CH$_2$COOH | 3 | O | m.p. 132–133° C. |
| (53) | H | 2-hydroxyphenyl | 2 | O | $n_D^{22.4}$ 1.5781 |
| (54) | CH$_3$ | phenyl | 3 | O | $n_D^{26.1}$ 1.5467 |
| (55) | CH$_3$ | —CH$_3$ | 3 | O | $n_D^{24.5}$ 1.4968 |
| (56) | H | —CCl=CClCOOH | 3 | O | m.p. 139–140° C. (dec.) |
| (57) | H | —CCl$_3$ | 3 | O | m.p. 104–105° C. |
| (58) | H | —CCl$_3$ | 3 | —NH | m.p. 85–87° C. |
| (59) | H | —CCl=CClCNH-(2-cycloheptenyl), C=O | 3 | O | m.p. 63–64° C. |
| (60) | H | —CH$_2$Cl | 3 | O | m.p. 92° C. |
| (61) | H | —CH$_2$-phenyl | 3 | O | m.p. 120° C. |
| (62) | H | —CH$_2$O-phenyl | 3 | O | m.p. 92° C. |
| (63) | H | 2,5-dimethylfuran-3-yl | 3 | O | m.p. 113–114° C. |

TABLE 2-continued

Present compounds represented by the formula

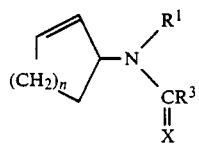

| Compound No. | R¹ | R³ | n | X | Physical constant |
|---|---|---|---|---|---|
| (64) | H | (phenyl) | 3 | O | m.p. 121° C. |
| (65) | H | (3-fluorophenyl) | 3 | O | m.p. 116° C. |
| (66) | H | (1-methylcyclopropyl) | 3 | O | m.p. 94° C. |
| (67) | H | (cyclohex-1-enyl) | 3 | O | m.p. 161° C. |
| (68) | H | —CH=CH₂ | 3 | O | m.p. 72–74° C. |
| (69) | H | —CH₂OCH₃ | 3 | O | m.p. 46–47° C. |
| (70) | H | (2-thienyl) | 3 | O | m.p. 147–148° C. |
| (71) | H | (1-naphthyl) | 3 | O | m.p. 170° C. |
| (72) | H | (3-chloro-4-nitrophenyl) | 3 | O | m.p. 154–156° C. |
| (73) | H | (2-methoxyphenyl) | 3 | O | m.p. 89–91° C. |
| (74) | H | —CH₂CH₂COOCH₃ | 3 | O | m.p. 65–67° C. |
| (75) | H | (2-carboxyphenyl) | 3 | O | m.p. 120–121° C. |
| (76) | H | —CH=CHCOOH | 3 | O | m.p. 114–115° C. |

TABLE 2-continued

Present compounds represented by the formula

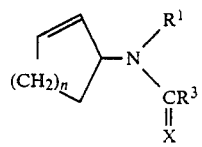

| Compound No. | R¹ | R³ | n | X | Physical constant |
|---|---|---|---|---|---|
| (77) | H | (3-pyridyl) | 3 | O | m.p. 97–98° C. |
| (78) | H | (2-quinoxalinyl) | 3 | O | $n_D^{23.9}$ 1.5910 |
| (79) | H | H | 3 | O | $n_D^{22.5}$ 1.5050 |
| (80) | H | (2-methylbenzofuran-3-yl) | 3 | O | m.p. 91° C. |
| (81) | H | —CHCl—phenyl | 3 | O | m.p. 120–121° C. |
| (82) | H | (3-methyl-4-nitro-phenoxyphenyl) | 3 | O | m.p. 132–134° C. |
| (83) | H | —C(=CH₂)CH₂—COO(CH₂)₂CH₃ | 3 | O | $n_D^{25.5}$ 1.4991 |
| (84) | H | (2,2-dichlorovinyl-3,3-dimethylcyclopropyl) | 3 | O | m.p. 117° C. |
| (85) | H | (3-chlorophenyl) | 3 | O | m.p. 117–118° C. |
| (86) | H | (4-methylphenyl) | 3 | O | m.p. 142° C. |
| (87) | H | (4-methoxyphenyl) | 3 | O | m.p. 145–147° C. |

TABLE 2-continued

Present compounds represented by the formula

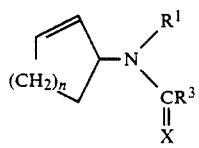

| Compound No. | R¹ | R³ | n | X | Physical constant |
|---|---|---|---|---|---|
| (88) | H | —C₆H₄—C₄H₉(t) (para) | 3 | O | m.p. 145–147° C. |
| (89) | H | —C₆H₄—Br (meta) | 3 | O | m.p. 137–138° C. |
| (90) | H | —C₆H₄—NO₂ (para) | 3 | O | m.p. 174° C. |
| (91) | H | —CH₂Br | 3 | O | m.p. 173–174° C. |
| (92) | H | —CH₂CH₂CH₃ | 3 | O | m.p. 76° C. |
| (93) | H | —C₆H₁₁ (cyclohexyl) | 3 | O | m.p. 168–169° C. |
| (94) | H | —C(CH₃)₃ | 3 | O | m.p. 119–120° C. |
| (95) | H | —CH₂CH₂Cl | 3 | O | m.p. 76–77° C. |
| (96) | H | —CH(CH₃)₂ | 3 | O | m.p. 138° C. |
| (97) | H | —C₅H₉ (cyclopentyl) | 3 | O | m.p. 150° C. |
| (98) | H | —CH₂C(CH₃)₃ | 3 | O | m.p. 132–133° C. |
| (99) | H | —CH₂Oiso-Bu | 3 | O | $n_D^{24.5}$ 1.4805 |
| (100) | H | —CH₂CH(CH₃)₂ | 3 | O | m.p. 117° C. |
| (101) | H | 2,2,3,3-tetramethylcyclopropyl | 3 | O | m.p. 120–122° C. |
| (102) | H | 1-phenylcyclopropyl | 3 | O | m.p. 156–158° C. |
| (103) | H | —C₆H₃(Cl)₂ (2,4-dichlorophenyl) | 3 | O | m.p. 181–182° C. |

TABLE 2-continued

Present compounds represented by the formula

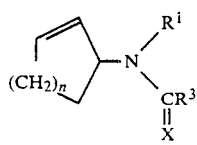

| Compound No. | R¹ | R³ | n | X | Physical constant |
|---|---|---|---|---|---|
| (104) | H | (3-cyanophenyl) | 3 | O | m.p. 133–135° C. |
| (105) | H | (2-furyl) | 3 | O | m.p. 103–105° C. |
| (106) | H | $-CH=CHOC_2H_5$ | 3 | O | m.p. 110–112° C. |
| (107) | $CH_2CN$ | $-CH_3$ | 3 | O | $n_D^{23.2}$ 1.5040 |
| (108) | $CH_2COOCH_3$ | $-CH_3$ | 3 | O | $n_D^{24.2}$ 1.4817 |
| (109) | H | (2-hydroxyphenyl) | 3 | O | $n_D^{23.1}$ 1.5770 |
| (110) | H | $-CH_2O-$(menthyl) | 3 | O | $n_D^{21.0}$ 1.4950 |
| (111) | H | $-CF=CH-$phenyl | 3 | O | m.p. 113° C. |
| (112) | H | $-CH_2-$(2,3-dihydro-1,4-benzodioxinyl) | 3 | O | m.p. 143° C. |
| (113) | H | $-CH_2S-$phenyl | 3 | O | m.p. 92° C. |
| (114) | H | (1H-pyrrol-2-yl) | 3 | O | m.p. 176° C. |
| (115) | H | (4-dimethylaminophenyl) | 3 | O | m.p. 126° C. |

TABLE 2-continued

Present compounds represented by the formula

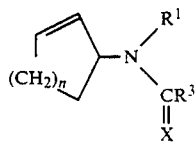

| Compound No. | R¹ | R³ | n | X | Physical constant |
|---|---|---|---|---|---|
| (116) | H | −C(=O)−C₆H₅ | 3 | O | m.p. 93° C. |
| (117) | −CH₂CH=CH₂ | −CH₃ | 3 | O | $n_D^{23.7}$ 1.5021 |
| (118) | cyclopropyl | −CH₃ | 3 | O | $n_D^{23.5}$ 1.5076 |
| (119) | −CH₂C≡CH | −CH₃ | 3 | O | $n_D^{28.5}$ 1.5131 |
| (120) | cycloheptenyl | −CH₃ | 3 | O | $n_D^{20.7}$ 1.5162 |
| (121) | −CH₂−(2-F-C₆H₄) | −CH₃ | 3 | O | $n_D^{25.3}$ 1.5329 |
| (122) | −CH₂CH₂OCH₂CH₃ | −CH₃ | 3 | O | $n_D^{23.3}$ 1.4850 |
| (123) | H | −CH₃ | 3 | O | J. Org. Chem. 46, 4727 (1981) |
| (124) | H | −CH₂O−(4-Cl-2-CH₃-C₆H₃) | 3 | O | m.p. 118° C. |
| (125) | cycloheptenyl | −CH₂Cl | 3 | O | $n_D^{24.8}$ 1.5373 |
| (126) | H | −CH₂CN | 3 | O | m.p. 131° C. |
| (127) | −CH(CH₃)₂ | −CH₂Cl | 3 | O | $n_D^{23.3}$ 1.5044 |
| (128) | cycloheptenyl | −CH(C₆H₅)₂ | 3 | O | m.p. 147° C. |

TABLE 2-continued

Present compounds represented by the formula

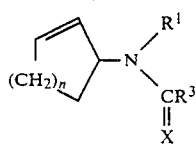

| Compound No. | R¹ | R³ | n | X | Physical constant |
|---|---|---|---|---|---|
| (129) | H | —CH(C₆H₅)₂ | 3 | O | m.p. 153° C. |
| (130) | —CH₂CH₂OCH₂CH₃ | —CH₂Cl | 3 | O | $n_D^{26.6}$ 1.5000 |
| (131) | H | (dihydrothiopyran/oxa CH₃ group) | 3 | O | m.p. 123° C. |
| (132) | (cycloheptenyl) | —CHCl₂ | 3 | O | $n_D^{26.1}$ 1.5467 |
| (133) | H | —(CH₂)₄Cl | 3 | O | m.p. 71° C. |
| (134) | —(CH₂)₅Cl | —CH₃ | 3 | O | $n_D^{22.5}$ 1.4966 |
| (135) | | —CH₂CH₂CH₂— | 3 | O | $n_D^{24.3}$ 1.5175 |
| (136) | —CHCH₃COOCH₃ | —CH₂OCH₃ | 3 | O | $n_D^{23.7}$ 1.4886 |
| (137) | H | 3,5-bis(CF₃)phenyl | 3 | O | m.p. 126° C. |
| (138) | H | —CH₂CH₃ | 2 | O | m.p. 80–82° C. |
| (139) | H | —CH₂CH₂COOH | 2 | O | m.p. 143–144° C. |
| (140) | H | —CH=CHCOOH | 2 | O | m.p. 113–114° C. |
| (141) | H | (dimethyl furan group) | 2 | O | m.p. 91–93° C. |
| (142) | H | —CH₂—C₆H₅ | 2 | O | m.p. 108–111° C. |
| (143) | H | 2-chlorophenyl | 2 | O | m.p. 128–130° C. |

TABLE 2-continued
Present compounds represented by the formula
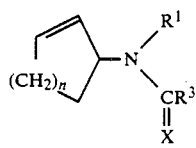
| Compound No. | R¹ | R³ | n | X | Physical constant |
|---|---|---|---|---|---|
| (144) | H | ![3-chlorophenyl] | 2 | O | m.p. 113–114° C. |
| (145) | H | ![4-chlorophenyl] | 2 | O | m.p. 162–164° C. |
| (146) | H | ![2-methylphenyl] | 2 | O | m.p. 118–120° C. |
| (147) | H | ![3-methylphenyl] | 2 | O | m.p. 90–92° C. |
| (148) | H | ![4-methylphenyl] | 2 | O | m.p. 133–135° C. |
| (149) | H | ![2-methoxyphenyl] | 2 | O | $n_D^{25.3}$ 1.5568 |
| (150) | H | ![3-methoxyphenyl] | 2 | O | m.p. 101–103° C. |
| (151) | H | ![4-methoxyphenyl] | 2 | O | m.p. 120–122° C. |
| (152) | H | ![2,6-dimethylphenyl] | 2 | O | m.p. 160–162° C. |

TABLE 2-continued

Present compounds represented by the formula

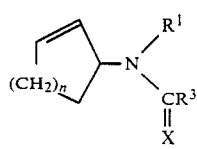

| Compound No. | R¹ | R³ | n | X | Physical constant |
|---|---|---|---|---|---|
| (153) | H | 2,4-dichlorophenyl | 2 | O | m.p. 143–145° C. |
| (154) | —CH₂CH₃ | —CH₃ | 2 | O | $n_D^{20.1}$ 1.4840 |
| (155) | H | 2-furyl | 2 | O | m.p. 86–87° C. |
| (156) | H | 3-furyl | 2 | O | m.p. 116–118° C. |
| (157) | H | 3-(trifluoromethyl)phenyl | 2 | O | m.p. 122–123° C. |
| (158) | H | 3-methyl-2-furyl | 2 | O | m.p. 115–116° C. |
| (159) | H | —CH(CH₃)₂ | 2 | O | m.p. 107–108° C. |
| (160) | H | —(CH₂)₁₂CH₃ | 2 | O | m.p. 82–83° C. |
| (161) | H | cyclohexyl | 2 | O | m.p. 165–166° C. |
| (162) | H | —CH₂C(CH₃)₃ | 2 | O | m.p. 118–121° C. |
| (163) | H | cyclobutyl | 2 | O | m.p. 107–108° C. |
| (164) | H | cyclopropyl | 2 | O | m.p. 125–126° C. |
| (165) | H | —CH=CHCH₃ | 2 | O | m.p. 86–89° C. |
| (166) | H | —CH₂C(=CH₂)COOH | 2 | O | m.p. 140–141° C. |
| (167) | H | 2-(trifluoromethyl)phenyl | 2 | O | m.p. 116–119° C. |
| (168) | H | —CHCl₂ | 2 | O | m.p. 128–129° C. |

TABLE 2-continued

Present compounds represented by the formula

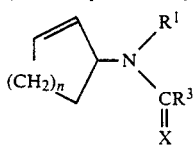

| Compound No. | R¹ | R³ | n | X | Physical constant |
|---|---|---|---|---|---|
| (169) | H | (CH₃/CH₃ substituted 1,4-oxathiane) | 2 | O | m.p. 94–95° C. |
| (170) | H | 4-pyridyl | 2 | O | m.p. 115–120° C. |
| (171) | —CH$_2$CN | —CH$_2$Cl | 2 | O | $n_D^{17.3}$ 1.4855 |
| (172) | —CH$_2$—C$_6$H$_4$—Cl (p) | —CH$_2$Cl | 2 | O | $n_D^{17.6}$ 1.5650 |
| (173) | —CH$_2$COOCH$_3$ | —CH$_2$Cl | 2 | O | $n_D^{17.5}$ 1.5070 |
| (174) | H | —CH$_2$—C$_6$H$_5$ | 1 | O | m.p. 116–117° C. |
| (175) | H | —CH$_2$—C$_6$H$_5$ | 4 | O | m.p. 157–158° C. |
| (176) | H | —CH$_2$—C$_6$H$_4$—CH$_3$ (p) | 2 | O | m.p. 134–135° C. |
| (177) | H | —CH$_2$—C$_6$H$_4$—CH$_3$ (m) | 2 | O | m.p. 90–91° C. |
| (178) | H | —CH$_2$—C$_6$H$_4$—CH$_3$ (o) | 2 | O | m.p. 141–142° C. |
| (179) | H | —CH$_2$—C$_6$H$_4$—Cl (o) | 2 | O | m.p. 150–151° C. |
| (180) | H | —C$_6$H$_4$(CH$_3$)(COOH) | 2 | O | m.p. 136–138° C. |

TABLE 2-continued

Present compounds represented by the formula

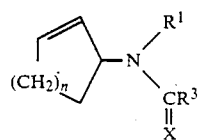

| Compound No. | R[1] | R[3] | n | X | Physical constant |
|---|---|---|---|---|---|
| (181) | H | —CH$_2$OCH$_3$ | 2 | O | n$_D^{25.5}$ 1.4866 |
| (182) | H | —CH$_2$O—C$_6$H$_5$ | 2 | O | m.p. 62–63° C. |
| (183) | H | —CH$_2$O—(menthyl) | 2 | O | n$_D^{20.5}$ 1.4920 |
| (184) | H | =CHCl—C$_6$H$_5$ | 2 | O | m.p. 109–112° C. |
| (185) | H | —CH$_2$—C$_6$H$_4$Cl (m) | 2 | O | m.p. 110–111° C. |
| (186) | H | —CH$_3$ | 2 | O | J. Am. Chem. Soc., 94, 7892 (1972) |
| (187) | H | —CH$_2$Cl | 2 | O | Can. J. Chem. 55, 700 (1977) |
| (188) | H | —C(CH$_3$)$_3$ | 2 | O | J. Am. Chem. Soc. 89, 6303 (1967) |
| (189) | H | —C$_6$H$_5$ | 2 | O | J. Am. Chem. Soc. 80, 4312 (1958) |
| (190) | H | —CCl$_3$ | 2 | O | J. Am. Chem. Soc. 98, 2901 (1976) |
| (191) | H | —CH=CHCl | 2 | O | m.p. 87–88° C. |
| (192) | H | H | 2 | O | n$_D^{20.0}$ 1.5050 |
| (193) | H | —CH$_2$CN | 2 | O | m.p. 110–115° C. |
| (194) | H | —CH$_2$S—C$_6$H$_5$ | 2 | O | m.p. 67–68° C. |
| (195) | H | —(1-naphthyl) | 2 | O | m.p. 153–156° C. |
| (196) | H | —CCl$_3$ | 2 | NH | Ger. Offen. 2,601,137 |
| (197) | H | —CF$_2$CF$_3$ | 2 | O | m.p. 72–73° C. |

TABLE 2-continued

Present compounds represented by the formula

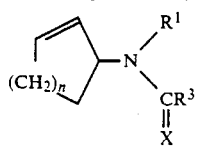

| Compound No. | R¹ | R³ | n | X | Physical constant |
|---|---|---|---|---|---|
| (198) | H | —⟨C₆H₄⟩—F | 2 | O | m.p. 120–122° C. |
| (199) | H | —⟨cyclohexenyl⟩ | 2 | O | m.p. 170–172° C. |
| (200) | H | —⟨N-methylpyrrolyl⟩ | 2 | O | m.p. 85–86° C. |
| (201) | H | —⟨quinoxalinyl⟩ | 2 | O | m.p. 70–75° C. |
| (202) | H | —CH₂—⟨C₆H₄⟩—Cl | 2 | O | m.p. 138–139° C. |
| (203) | H | —CH₃ | 2 | S | m.p. 57–59° C. |
| (204) | H | —⟨thienyl⟩ | 2 | O | m.p. 129–130° C. |
| (205) | H | —⟨C₆H₄⟩—C(CH₃)₃ | 2 | S | m.p. 88–91° C. |
| (206) | H | ⟨cyclopropyl with CH₃ CH₃⟩—COOH | 2 | O | Resinous product |
| (207) | H | —CCl=CClCOOH | 2 | O | m.p. 106–109° C. |
| (208) | —CH(CH₃)COOCH₃ | —CH₂Cl | 2 | O | $n_D^{24.0}$ 1.5090 |
| (209) | H | —CH₂N⟨imidazolyl⟩ | 2 | O | m.p. 108–110° C. |
| (210) | H | —CH₂N⟨1,2,4-triazolyl⟩ | 2 | O | m.p. 152° C. |
| (211) | H | —⟨C₆H₄⟩—I | 2 | O | m.p. 110–112° C. |

TABLE 2-continued

Present compounds represented by the formula

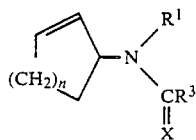

| Compound No. | R¹ | R³ | n | X | Physical constant |
|---|---|---|---|---|---|
| (212) |  | —CH₂CH₂CH₂— | 2 | O | $n_D^{26.5}$ 1.5101 |
| (213) |  | 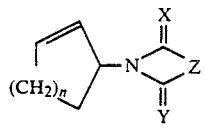 | 2 | O | $n_D^{24.8}$ 1.6314 |

Method (h)

When the present compound is an acid imide compound represented by the formula (XX),

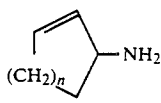 (XX)

wherein X, Y, Z and n represent the same meanings as above, provided that a case wherein when n is 2 or 3 and X and Y are an oxygen atom, Z is an o-phenylene group, is excluded, it can be produced by reacting cycloalkenylamine represented by the formula (XXI),

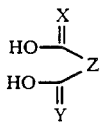 (XXI)

wherein n represents the same meaning as above, with 0.9 to 1.0 equivalent of a compound represented by the formula (XXII),

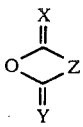 (XXII)

wherein X, Y and Z represent the same meanings as above, or its anhydride, i.e. a compound represented by the formula (XXIII),

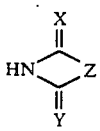 (XXIII)

wherein X, Y and Z represent the same meanings as above, with or without a solvent at 80° to 180° C., preferably 130° to 160° C. for 1 to 30 hours in the presence or absence of a catalyst.

As the compound represented by the formula (XXII), there are given for example succinic acid, 1,2-cyclohexanedicarboxylic acid, maleic acid, citraconic acid, isopropylidenesuccinic acid, 3,4,5,6-tetrahydrophthalic acid, mellitic acid, 4-carboxyphthalic acid, dichloromaleic acid, phenylmaleic acid, tetrachlorophthalic acid, tetrabromophthalic acid, 3-nitrophthalic acid, 1,2-pyridinedicarboxylic acid, 3,4-furandicarboxylic acid, glutaric acid, 2,2-dimethylglutaric acid, 3,4-pyrazinedicarboxylic acid, 3,3-dimethylglutaric acid, dimethylmaleic acid, naphthalic acid, 1,2-cyclobutanedicarboxylic acid monochloromaleic acid, monobromomaleic acid, dibromomaleic acid, monofluoromaleic acid, difluoromaleic acid, malic acid, thiomalic acid methoxysuccinic acid, 2-methyl-2-phenylsuccinic acid, acetoxysuccinic acid, acetylthiosuccinic acid, tetrafluorophthalic acid, 5-norbornane-2,3-dicarboxylic acid, 1,2-dimethyl-1,2-cyclopropanedicarboxylic acid, itaconic acid, camphanic acid, diphenic acid, diphenylcarbamoyloxysuccinic acid, phenylcarbamoyloxysuccinic acid, cis, cis, cis, cis-1,2,3,4-cyclopentanetetracarboxylic acid, bicyclo[2,2,2]octa-5-ene-2,3-dicarboxylic acid and the like. As the compound represented by the formula (XXIII), there are given the anhydrides of the compounds represented by the foregoing formula (XXII).

Method (i)

When the present compound is an acid imide compound represented by the foregoing formula (XX) (provided that a case wherein when n is 1, 2 or 3 and X and Y are an oxygen atom, Z is an o-phenylene group, is excluded), it can be produced by reacting a compound represented by the foregoing formula (VII) with 1.0 to 1.1 equivalent of a compound represented by the formula (XXIV),

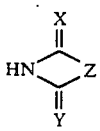 (XXIV)

wherein X, Y and Z represent the same meanings as above, with or without a solvent at 0° to 200° C., preferably 20° to 160° C. for 1 to 24 hours in the presence of 1.0 to 1.1 equivalent of an acid-binding agent.

As the compound represented by the formula (XXIV), there are given for example acid imides corresponding to the compounds represented by the foregoing formula (XXIII) and the compounds described below:
5,5-Dimethyl-2-thioxo-4-oxazolidinone
5,5-Dimethyl-4-thioxo-2-oxazolidinone
5,5-Dimethyl-2,4-thiazolidinedione
2-Thioxo-4-imidazolidinone
2,4-Imidazolidinedione
5,5-Dimethyl-2,4-oxazolidinedione
5,5-Dimethyl-2-thioxo-4-imidazolidinone
5,5-Dimethyl-2,4-imidazolidinedione
5,5-Dimethyl-2-thioxo-4-thiazolidinone
5-Imino-2-pyrrolidinone Method (j)

When the present compound is an acid imide compound represented by the formula (XXV),

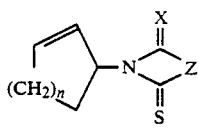
(XXV)

wherein X, Z and n represent the same meanings as above, it can be produced by reacting an acid imide compound represented by the formula (XXVI),

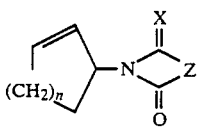
(XXVI)

wherein X, Z and n represent the same meanings as above, with 1 or 2 equivalents of phosphorus pentasulfide at 25° C. to 150° C. for 1 to 24 hours in the presence or absence of a solvent.

The acid imide compound represented by the formula (XXVI) is obtained by the foregoing method.

The solvent used in the methods (h) to (j) includes for example aliphatic hydrocarbons such as hexane, heptane, ligroin, petroleum ether, etc., aromatic hydrocarbons such as benzene, toluene, xylene, etc., halogenated hydrocarbons such as chloroform, carbon tetrachloride, dichloroethane, chlorobenzene, dichlorobenzene, etc., ethers such as diethyl ether, diisopropyl ether, dioxane, tetrahydrofuran, diethylene glycol dimethyl ether, etc., fatty acids such as formic acid, acetic acid, oleic acid, etc., alcohols such as methanol, ethanol, isopropanol, tert-butanol, octanol, cyclohexanol, methyl cellosolve, diethylene glycol, glycerin, etc., nitro compounds such as nitroethane, nitrobenzene, etc., nitriles such as acetonitrile, isobutyronitrile, etc., tertiary amines such as pyridine, triethylamine N,N-diethylaniline, tributylamine, N-methylmorpholine, etc., sulfur compounds such as dimethyl sulfoxide, sulfolane, etc., water and mixtures thereof.

Also, the acid-binding agent includes for example organic bases such as pyridine, triethylamine, N,N-diethylaniline, etc. and inorganic bases such as sodium carbonate, potassium carbonate, sodium hydrogencarbonate, potassium hydroxide, sodium hydroxide, sodium hydride, etc.

After completion of the reaction, the reaction solution is after-treated as usual, for example an organic solvent is added to the solution which is then washed with an alkali and water to obtain the objective compound. If necessary, the compound obtained is purified by chromatography, distillation, recrystallization and the like.

Next, examples of production of the present compound by the methods (h) to (j) will be shown.

PRODUCTION EXAMPLE 10

A mixture of 2-cycloheptenylamine (1.01 g), succinic anhydride (1.0 g) and acetic acid (10 ml) was heated under reflux for 24 hours. After cooling, ether (20 ml) was added to the reaction mixture which was then washed with a saturated aqueous sodium hydrogencarbonate solution, water and a saturated aqueous sodium chloride solution in this order. The organic layer was dried over anhydrous magnesium sulfate and concentrated. The oily product thus obtained was purified by column chromatography on silica gel to obtain 1.07 g of N-(2-cycloheptenyl)succinimide [[Compound (214)]].
$n_D^{24.3}$ 1.4872

PRODUCTION EXAMPLE 11

A mixture of N-2-cycloheptenyl-3,4,5,6-tetrahydrophthalimide (3.75 g), phosphorus pentasulfide (3,40 g) and toluene (10 ml) was heated under reflux for 5 hours. The reaction mixture was cooled, poured into water and extracted with ether. The organic layer was dried over anhydrous magnesium sulfate and concentrated. The oil obtained was purified by column chromatography on silica gel to obtain 1.51 g of the objective compound [Compound (215)].
$n_D^{22.5}$ 1.6604

PRODUCTION EXAMPLE 12

A mixture of 2-cycloheptenylamine (1.11 g), 1,2-dimethyl-1,2-cyclopropanedicarboxylic acid (1.58 g) and toluene (30 ml) was heated, and formed water was removed azeotropically. Thereafter, the mixture was concentrated, and the oily product obtained was purified by chromatography on silica gel to obtain 1.26 g of N-(2-cycloheptenyl)- 1,2-dimethyl-1,2-cyclopropanedicarboxyimide [Compound (216)].
m.p. 57°-59° C.

PRODUCTION EXAMPLE 13

A mixture of 2-cycloheptenylamine (1.01 g), dichloromaleic anhydride (1.67 g) and acetic acid (10 ml) was heated under reflux for 3 hours. After cooling, ether (20 ml) was added to the reaction mixture which was then washed with a saturated aqueous sodium hydrogencarbonate solution, water and a saturated aqueous sodium chloride solution in this order. The organic layer was dried over anhydrous magnesium sulfate and concentrated. The deposited crystal was purified by recrystallization from hexane to obtain 1.67 g of N-(2-cycloheptenyl)dichloromaleinimide [Compound (217)].
m.p. 90°-91° C.

PRODUCTION EXAMPLE 14

3-Bromocycloheptene (1.75 g) was added dropwise at room temperature to a DMF suspension (10 ml) of sodium succinimide prepared from succinimide (0.99 g) and 60% sodium hydride (0.40 g). This mixture was stirred at room temperature for 24 hours, poured into water (10 ml) and extracted with ether. The oily product obtained by concentration was purified by chromatography on silica gel to obtain 0.09 g of N-(2-cycloheptenyl)succinimide [Compound (214)].
$n_D^{24.2}$ 1.4875

Some of the present compounds similarly obtained are shown collectively in Table 3.

TABLE 3

Present compounds represented by the formula,

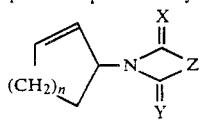

| Compound No. | X | Y | Z | n | Physical constant |
|---|---|---|---|---|---|
| (214) | O | O | —CH$_2$CH$_2$— | 3 | $n_D^{24.3}$ 1.4872 |
| (215) | S | S | (cyclohexene-diyl) | 3 | $n_D^{22.5}$ 1.6004 |
| (216) | O | O | (cyclopropane with two CH$_3$) | 3 | m.p. 57–59° C. |
| (217) | O | O | —CCl=CCl— | 3 | m.p. 90–91° C. |
| (218) | O | O | —S—C(CH$_3$)$_2$— | 3 | m.p. 86–88° C. |
| (219) | O | O | —CBr=CBr— | 3 | m.p. 134–135° C. |
| (220) | O | O | —CCl=CH— | 3 | m.p. 100° C. |
| (221) | O | O | —CBr=CH— | 3 | m.p. 114–116° C. |
| (222) | O | O | —CH=CH— | 3 | $n_D^{25.9}$ 1.5732 |
| (223) | O | O | —C(CH$_3$)=CH— | 3 | $n_D^{22.6}$ 1.5748 |
| (224) | O | O | —C(=CH$_2$)CH$_2$— | 3 | $n_D^{22.6}$ 1.5862 |
| (225) | O | O | —C(=C(CH$_3$)$_2$)CH$_2$— | 3 | $n_D^{19.3}$ 1.5892 |
| (226) | O | O | (nitrobenzene-diyl) | 3 | m.p. 175–177° C. |
| (227) | O | O | (pyridine-diyl) | 3 | m.p. 156° C. |
| (228) | O | O | (cyclohexane-diyl) | 3 | m.p. 81–83° C. |
| (229) | O | O | (phenyl-CH=CH$_2$ substituent) | 3 | m.p. 84–86° C. |
| (230) | O | O | —CH$_2$—CH(OH)— | 3 | m.p. 121–123° C. |
| (231) | O | O | —CH$_2$CH(SH)— | 3 | m.p. 64–67° C. |
| (232) | O | O | —CH$_2$CH(OCH$_3$)— | 3 | $n_D^{33.0}$ 1.5621 |
| (233) | O | O | —CH$_2$CH(OC(=O)CH$_3$)— | 3 | m.p. 86–88° C. |

TABLE 3-continued

Present compounds represented by the formula,

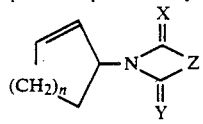

| Compound No. | X | Y | Z | n | Physical constant |
|---|---|---|---|---|---|
| (234) | O | O | —CH$_2$CH(SC(=O)CH$_3$)— | 3 | m.p. 93–95° C. |
| (235) | O | O | (cyclobutane-1,2-diyl) | 3 | $n_D^{21.7}$ 1.5741 |
| (236) | O | O | (norbornene-2,3-diyl) | 3 | $n_D^{25.3}$ 1.5329 |
| (237) | O | O | —C(CH$_3$)CH$_2$— (with phenyl) | 3 | $n_D^{22.5}$ 1.5505 |
| (238) | S | O | —NHCH$_2$— | 3 | m.p. 148° C. |
| (239) | O | O | (cyclohexene-1,2-diyl) | 3 | m.p. 102° C. |
| (240) | O | O | —C(CH$_3$)=C(CH$_3$)— | 3 | $n_D^{27.4}$ 1.5689 |
| (241) | O | O | —CH{OCN(—C$_6$H$_4$—)$_2$}CH$_2$— | 3 | m.p. 53° C. |
| (242) | S | O | —S—CH$_2$— | 3 | $n_D^{22.0}$ 1.5535 |
| (243) | O | O | (tetrafluorobenzene-1,2-diyl) | 3 | m.p. 173–174° C. |
| (244) | O | O | (benzene-1,2-diyl) | 3 | Eur. J. Med. Chem. 13, 81 (1978) |
| (245) | O | O | —CH$_2$CH$_2$— | 2 | $n_D^{28.2}$ 1.5192 |
| (246) | O | O | —CH=CH— | 2 | $n_D^{23.6}$ 1.5211 |
| (247) | O | O | —CCl=CCl— | 2 | m.p. 89° C. |
| (248) | O | O | (cyclohexadiene-1,2-diyl) | 2 | Chem. & Ind. 414, (1958) |
| (249) | O | O | (cyclohexene-1,2-diyl) | 2 | m.p. 46–48° C. |

TABLE 3-continued

Present compounds represented by the formula,

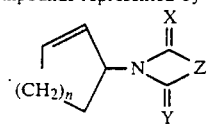

| Compound No. | X | Y | Z | n | Physical constant |
|---|---|---|---|---|---|
| (250) | O | O | (2,3-dimethylcyclohex-1-enyl) | 1 | m.p. 41–44° C. |
| (251) | O | O | —C(CH$_3$)=CH— | 4 | $n_D^{20.4}$ 1.5227 |
| (252) | O | O | —C(=CH$_2$)CH$_2$— | 4 | $n_D^{20.4}$ 1.5331 |
| (253) | O | S | (2,3-dimethylcyclohex-1-enyl) | 2 | m.p. 45–48° C. |
| (254) | O | O | —C(=C(CH$_3$)$_2$)CH$_2$— | 2 | $n_D^{18.2}$ 1.5361 |
| (255) | O | O | (2,3-dimethyl-nitrobenzene) | 2 | m.p. 100–101° C. |
| (256) | O | O | (2,3-disubstituted pyridine) | 2 | m.p. 76° C. |
| (257) | O | O | (1,2-disubstituted cyclohexane) | 2 | m.p. 67° C. |
| (258) | O | O | —C(=CH$_2$)—(phenyl) | 2 | m.p. 140° C. |
| (259) | O | O | —CCl=CCl— | 4 | m.p. 63–64° C. |
| (260) | O | O | (2,2-dimethylcyclopropane-1,3-diyl) | 2 | $n_D^{25.0}$ 1.5079 |
| (261) | O | O | —OC(CH$_3$)$_2$— | 2 | m.p. 69–71° C. |
| (262) | O | S | —NHCH$_2$— | 2 | m.p. 106–108° C. |
| (263) | O | O | —CH=CCl— | 2 | m.p. 78° C. |
| (264) | O | O | —CH=CBr— | 2 | m.p. 90–91° C. |
| (265) | O | O | —C(CH$_3$)=CH— | 2 | m.p. 65–66° C. |
| (266) | O | O | —CCl=CCl— | 1 | m.p. 52° C. |
| (267) | O | O | —NHCH$_2$— | 2 | m.p. 91° C. |
| (268) | O | O | —C(CH$_3$)=C(CH$_3$)— | 2 | $n_D^{25.2}$ 1.5178 |
| (269) | O | O | —CH$_2$CH(SCOOCH$_3$)— | 2 | $n_D^{29.5}$ 1.5344 |
| (270) | O | O | (cyclobutane-1,2-diyl) | 2 | $n_D^{29.5}$ 1.5220 |

TABLE 3-continued

Present compounds represented by the formula,

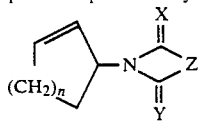

| Compound No. | X | Y | Z | n | Physical constant |
|---|---|---|---|---|---|
| (271) | O | O | (bicyclic structure with two methyl groups) | 2 | m.p. 97° C. |
| (272) | O | O | —CH(OH)CH$_2$— | 2 | m.p. 108-110° C. |
| (273) | O | O | —CH(OCOCH$_3$)CH$_2$— | 2 | m.p. 96° C. |
| (274) | O | O | —CH(OCH$_3$)CH$_2$— | 2 | $n_D^{30.7}$ 1.5110 |
| (275) | O | O | —CH(SH)CH$_2$— | 2 | $n_D^{29.7}$ 1.5490 |
| (276) | O | O | —CH(OCNH—⟨phenyl⟩—)CH$_2$— (with C=O) | 2 | m.p. 165-168° C. |
| (277) | O | O | —CBr=CBr— | 2 | m.p. 81° C. |

Method (k)

When the present compound is an imine compound represented by the formula (XXVII),

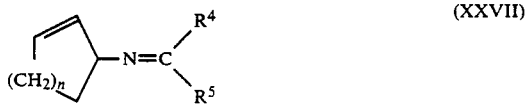

wherein $R^4$, $R^5$ and n represent the same meanings as above, provided that the following cases are excluded: when n is 1, $R^4$ is a butyl group and $R^5$ is a pentyl group, or $R^4$ and $R^5$, taken together, form a 2,4,4-trimethyl-1-pentenylene group; and when n is 2, $R^4$ and $R^5$, taken together, form a pentenylene group, it can be produced by reacting cycloalkenylamine represented by the foregoing formula (XXI) with 0.95 to 1.0 equivalent of a carbonyl compound represented by the formula (XXVIII),

wherein $R^4$ and $R^5$ represent the same meanings as above, at 0° to 150° C. for 1 to 24 hours with or without a solvent.

As the carbonyl compound represented by the above formula (XXVIII), there are given for example formaldehyde, acetaldehyde, propionaldehyde, glyoxylic acid, methoxyacetaldehyde, butylaldehyde, isobutylaldehyde, n-valeraldehyde, isovaleraldehyde, 2-methylbutylaldehyde, hexanal, heptanal, octanal, decanal, β-phenylpropionaldehyde dodecanal, 5-norbornane-2-carboaldehyde, cyclohexanecarboaldehyde, cyclooctanecarboaldehyde, 2-ethylbutanal, phenylacetaldehyde, chloroacetaldehyde, chloral, cinnamaldehyde, α-methylcinnamaldehyde, α-bromocinnamaldehyde, α-chlorocinnamaldehyde, acrolein, acrolein dimer, metacrolein, crotonaldehyde, trans-2-hexenylaldehyde, 2-ethyl-2-butenal, 2-ethylhexanal, citral, citronellal, phenylpropargylaldehyde, DL-glyceraldehyde, aldol, glyoxal, terephthalaldehyde, benzaldehyde, o-fluorobenzaldehyde, α,α,α-trifluoro-m-tolualdehyde, pentafluorobenzaldehyde, m-bromobenzaldehyde, 3,5-diiodo-4-hydroxybenzaldehyde, o-chlorobenzaldehyde, 3,5-dichlorobenzaldehyde, 3,5-dichlorosalicylaldehyde, 2-chloro-6-fluorobenzaldehyde, 2,3,6-trichlorobenzaldehyde, 2,5-dichloro-4-nitrobenzaldehyde, 2,4,5-trichloro-3-nitrobenzaldehyde, salicylaldehyde, 5-bromosalicylaldehyde, vanillin, 2-carboxybenzaldehyde 5-chlorosalicylaldehyde, p-methylthiobenzaldehyde, 4-hydroxy-3,5-dimethoxybenzaldehyde, 3-ethoxy-4-hydroxybenzaldehyde, 5-nitrosalicylaldehyde, 4-hydroxy-3,5-di-tert-butylbenzaldehyde, p-anisaldehyde, 2,5-dimethoxybenzaldehyde, m-[m-(trifluoromethyl)phenoxy]benzaldehyde, 5-bromo-o-anisaldehyde, 3-chloro-4-hydroxy-5-ethoxybenzaldehyde, 4-hydroxy-5-bromo-m-anisaldehyde, o-ethoxybenzaldehyde, 2,3-dimethyl-4-methoxybenzaldehyde, 4-[β-(diethylamino)ethoxy]benzaldehyde, piperonal, 6-nitropiperonal, 3-methyl-p-anisaldehyde, m-(p-chlorophenoxy)benzaldehyde, 3-benzyloxybenzaldehyde, p-phenoxybenzaldehyde, 3,4,5-trimethoxybenzaldehyde, methyl 4-formylbenzoate, o-nitrobenzaldehyde, p-nitrobenzaldehyde, 4-chloro-3-nitrobenzaldehyde, 3-methoxy2-nitrobenzaldehyde, 4-fluoro-2-nitrobenzaldehyde, 5-hydroxy-2-nitrobenzaldehyde, pg,64 p-cyanobenzaldehyde, 2,4-dimethylbenzaldehyde, o-tolualdehyde, cuminaldehyde, α-naphthaldehyde, p-phenylbenzaldehyde p-dimethylaminobenzaldehyde, 5-formyl-2-furansulfonic acid, p-acetaminobenzaldehyde, 5-methylfurfural, 2-thiophenecarboaldehyde, β-2-furylacrolein, nicotinaldehyde, furfural, 5-nitrofurfural, 5-methyl-2-thiophenecarboaldehyde, N-methylpyrrole-2-carboaldehyde, chloroacetone, bromoacetone, hydroxyacetone, α,α'-dichloroacetone, hexachloroacetone, methyl ethyl ketone, methyl vinyl ketone, diacetyl, 3-chloro-2-butanone, cyclobutanone, acetoin, methoxyacetone, perchloro 2-cyclobuten -1-one, 3-methyl-2-butanone, 2- pentanone, cyclopentanone, 3-penten-2-one, acetylacetone, pinacolone, bromopinacolone, 3-hexanone, mesityl oxide, 4-methyl-2-pentanone, acetonylacetone, cyclohexanone, 1,2-cyclohexanedione, 1,4-cyclohexanedione, 2-cyclo-hexen-1-one, 3-methyl-2-cyclopenten-1-one, 3-methylcyclopentanone, 2-methyl-1,3-cyclopentanedione, 3-acetylfuran, 1-hexen-5-one, 2-hydroxy-3-methyl-2-cyclopenten-1-one, methyl 1-methylcyclopropyl ketone, 2-methylcyclohexanone, 2-methyl-1,3-cyclohexanedione, 5-methyl-2-hexanone, 2-heptanone, dimedone, 2-octanone, 2-methyl-2-hepten-6-one, 3,5-dimethyl-2-cyclohexen-1-one, isophorone, phorone, 2,6-dimethyl-4-heptanone, 4-tert-butylcyclohexanone, menthone, l-carvone, β-ionone, DL-camphor, 6-methoxy-1-tetralone, 6-undecanone, 5-nonanone quinone, di-tert-butyl-p-quinone, 2,5-dichloro-p-benzoquinone, 2,3-dichloro-1,4-naphthoquinone, 2-hydroxy-1,4-naphthoquinone, 2-methyl-1,4-naphthoquinone, anthraquinone, phenanthrenequinone, 2,6-dihydroxyanthraquinone, acetophenone, o-hydroxyacetophenone, p-nitroaceto-phenone, m-chloroacetophenone, o-fluoroacetophenone, p-bromoacetophenone 2,4-dichloroacetophenone, 2,4-dihydroxyacetophenone, α,α-dichloroacetophenone, α-bromoacetophenone, 2,3,4-trichloroacetophenone, α-chloroacetophenone, p-methoxyacetophenone, o-methylacetophenone, α,α,α-trifluoroacetophenone, p-chlorophenacyl bromide, α-methoxyacetophenone, propiophenone, p-chloropropiophenone, p-fluoropropiophenone, 2-hydroxy-5-methylacetophenone, phenoxyacetone, 1-indanone, 1,3-indanedione, phenyl n-propyl ketone, α-bromoisobutyrophenone, phenyl propenyl ketone, o-hydroxybutyrophenone, benzoylacetone, 3,4-dimethylacetophenone, cyclopropyl phenyl ketone, benzalacetone, 4-methoxypropiophenone, 2,4,6-trimethylacetophenone, valerophenone, β-acetonaphthone, hexaphenone, 2-acetyl-1-tetralone, benzophenone, p-chlorobenzophenone, 2-chloro-5-nitrobenzophenone, 4-hydroxybenzophenone, 2,4-dihydroxybenzophenone, 5-chloro-2-hydroxybenzophenone, 9-fluorenone, benzoyl, benzil, deoxybenzoin, 4-acetylbiphenyl, p-phenyl-α-bromoacetophenone, acridone, 4-methoxy-2-hydroxybenzophenone, anthrone, dibenzoylmethane, benzalacetophenone, 2-hydroxychalcone, tetrahydrothiopyran-4-one, bis-3,4-methylenedioxybenzil, 2,2'-dihydroxy-4,4'-dimethoxylbenzophenone, 2'-carboxy-2-hydroxy-4-methoxybenzophenone, 2'-(o-chlorobenzoyl)-2,4'-dichloroacetanilide, 4,4'-bis(dimethylamino)benzophenone, 5,7-dichloroisatin, 6-chloroisatin, isatin, 5-nitroisatin 3-(hexahydro-1H-azepin-1-yl)-3'-nitropropiophenone, s-triazolo[4,3α]pyrido-3(2H)-one, perinaphthenone, thioxanthen-9-one, xanthone, 2-acetylpyridine, 3-benzoylpyridine, di-2-pyridyl ketone, dipyridylglyoxal, 3,5-diiodo-4-pyridone, 3-acetyl-2,4-dimethylpyrrole, pyrrole-2-carboaldehyde, 2,2,6,6-tetramethyl-4-piperidone, 1-methyl-4-piperidone, methyl 4-oxo-3-piperidinecarboxylate and the like.

The solvent used in this method (k) includes for example aliphatic hydrocarbons such as hexane, heptane, ligroin, petroleum ether, etc., aromatic hydrocarbons such as benzene, toluene, xylene, etc., halogenated hydrocarbons such as chloroform, carbon tetrachloride, dichloroethane, chlorobenzene, dichlorobenzene, etc., ethers such as diethyl ether, diisopropyl ether, dioxane, tetrahydrofuran, diethylene glycol dimethyl ether, etc., alcohols such as methanol, ethanol, isopropanol, tert-butanol, octanol, cyclohexanol, methyl cellosolve, diethylene glycol, glycerin, etc., esters such as ethyl formate, ethyl acetate, butyl acetate, diethyl carbonate, etc., nitro compounds such as nitroethane, nitrobenzene, etc., nitriles such as acetonitrile isobutyronitrile, etc., tertiary amines such as pyridine, triethylamine, N,N-diethylaniline, tributylamine, N-methylmorpholine, etc., acid amides such as formamide, N,N-dimethylformamide, acetamide, etc., sulfur compounds such as dimethyl sulfoxide, sulfolane, etc., water an mixtures thereof.

The catalyst used includes for example benzenesulfonic acid, p-toluenesulfonic acid, phosphoryl chloride, boron trifluoride, titanium tetrachloride and the like.

After completion of the reaction, the common aftertreatment is carried out and if necessary, the product obtained is purified by chromatography, distillation, recrystallization and the like.

Next, examples of production of the present compound by the method (k) will be shown.

PRODUCTION EXAMPLE 15

A mixture of 2-cycloheptenylamine (11.1 g, 0.1 mole), benzaldehyde (10.6 g, 0.1 mole) and benzene (50 ml) was heated under reflux, and resulting water was removed by azeotropic distillation. The mixture was concentrated to obtain 16.7 g of N-benzylidene-2-cycloheptenylamine [Compound (280)].

$n_D^{22.3}$ 1.5631

PRODUCTION EXAMPLE 16

A mixture of 2-cyclohexenylamine (9.7 g, 0.1 mole), cyclohexanone (9.8 g, 0.1 mole), zinc chloride (0.16 g) and benzene (50 ml) was heated under reflux, and resulting water was removed by azeotropic distillation. The mixture was concentrated and distilled to obtain 12.4 g of N-cyclohexylidene-2-cyclohexenylamine [Compound (344)].

b.p. 91°–93° C./2 mmHg

Some of the present compounds which can be produced by this method are shown in Table 4.

TABLE 4

Present compounds represented by the formula,

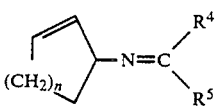

| Compound No. | R⁴ | R⁵ | n | Physical contant |
|---|---|---|---|---|
| (278) | H | 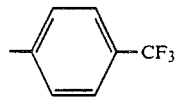 | 2 | $n_D^{24.1}$ 1.5135 |

TABLE 4-continued

Present compounds represented by the formula, $$\underset{(CH_2)_n}{\overset{\diagup}{\diagdown}}N=C\underset{R^5}{\overset{R^4}{\diagdown}}$$

| Compound No. | R[4] | R[5] | n | Physical contant |
|---|---|---|---|---|
| (279) | H | 2-fluorophenyl | 3 | $n_D^{23.7}$ 1.5476 |
| (280) | H | phenyl | 3 | $n_D^{22.3}$ 1.5631 |
| (281) | H | —CH$_2$CH(CH$_3$)CH$_2$CH$_2$—CH$_2$=C(CH$_3$)$_2$ | 3 | $n_D^{22.7}$ 1.4876 |
| (282) | H | cyclohexyl (H) | 3 | $n_D^{25.3}$ 1.5004 |
| (283) | H | —CH$_2$CH$_3$ | 3 | $n_D^{23.0}$ 1.4823 |
| (284) | H | —CH$_2$CH$_2$-phenyl | 3 | $n_D^{23.5}$ 1.5406 |
| (285) | H | 2-thienyl | 3 | $n_D^{24.2}$ 1.5855 |
| (286) | H | pyridyl | 3 | $n_D^{24.2}$ 1.5637 |
| (287) | H | 1-naphthyl | 3 | $n_D^{25.3}$ 1.6192 |
| (288) | H | biphenyl | 3 | $n_D^{24.2}$ 1.6279 |
| (289) | H | —CH$_2$CH$_2$CH$_2$CH$_3$ | 3 | $n_D^{24.3}$ 1.4797 |
| (290) | H | —CH$_2$OCH$_3$ | 3 | $n_D^{24.0}$ 1.4916 |
| (291) | H | —CH(CH$_3$)$_2$ | 3 | $n_D^{23.9}$ 1.4785 |
| (292) | H | 2-hydroxyphenyl | 3 | $n_D^{23.5}$ 1.5792 |
| (293) | H | —CCl=CH-phenyl | 3 | $n_D^{24.2}$ 1.5869 |

TABLE 4-continued
Present compounds represented by the formula,
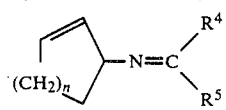
| Compound No. | R[4] | R[5] | n | Physical contant |
|---|---|---|---|---|
| (294) | H | —CH=CH—C₆H₅ | 3 | $n_D^{24.2}$ 1.5994 |
| (295) | H | —C≡C—C₆H₅ | 3 | $n_D^{23.0}$ 1.5919 |
| (296) | H | —C₆H₄—CH=N—(cycloheptenyl) (para) | 3 | m.p. 114–115° C. |
| (297) | H | —C₆H₄—CH₃ (ortho) | 3 | $n_D^{21.5}$ 1.5589 |
| (298) | H | —C₆H₄—OC₂H₅ (ortho) | 3 | $n_D^{21.9}$ 1.5532 |
| (299) | H | 2-furyl | 3 | $n_D^{22.2}$ 1.5502 |
| (300) | H | —C₆H₄—SCH₃ (para) | 3 | m.p. 42° C. |
| (301) | H | —C₆H₄—NO₂ (ortho) | 3 | $n_D^{23.5}$ 1.5725 |
| (302) | H | —C₆H₄—CN (para) | 3 | $n_D^{24.1}$ 1.5769 |
| (303) | H | —C₆H₄—O—C₆H₄—CF₃ | 3 | $n_D^{23.6}$ 1.5488 |
| (304) | —CH₂CH₂CH₂CH₂CH₂— | | 3 | b.p. 79–83° C./0.75 mm Hg |

TABLE 4-continued
Present compounds represented by the formula,
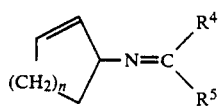
| Compound No. | $R^4$ | $R^5$ | n | Physical contant |
|---|---|---|---|---|
| (305) | H | (3-CF$_3$-phenyl) | 3 | $n_D^{23.6}$ 1.5116 |
| (306) | H | (4-COOCH$_3$-phenyl) | 3 | $n_D^{23.9}$ 1.5640 |
| (307) | —CH$_2$CH$_3$ | (phenyl) | 3 | b.p. 111–114° C./1.2 mm Hg |
| (308) | —CH$_2$C(CH$_3$)$_2$CH$_2$C(CH$_3$)=CH— | | 3 | b.p. 103–106° C./0.8 mm Hg |
| (309) | H | (phenyl) | 2 | $n_D^{27.0}$ 1.5692 |
| (310) | H | (3-CH$_3$-phenyl) | 2 | $n_D^{25.5}$ 1.5672 |
| (311) | H | (3-OH-phenyl) | 2 | $n_D^{27.1}$ 1.5839 |
| (312) | H | (3-F-phenyl) | 2 | $n_D^{26.8}$ 1.5519 |
| (313) | H | (3-OC$_2$H$_5$-phenyl) | 2 | $n_D^{25.4}$ 1.5610 |
| (314) | H | (4-NO$_2$-phenyl) | 2 | $n_D^{24.9}$ 1.5941 |
| (315) | H | (2-thienyl) | 2 | $n_D^{25.0}$ 1.5951 |

TABLE 4-continued

Present compounds represented by the formula,

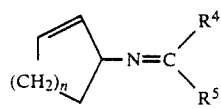

| Compound No. | R⁴ | R⁵ | n | Physical contant |
|---|---|---|---|---|
| (316) | H | -C₆H₄-CN (para) | 2 | $n_D^{25.3}$ 1.5850 |
| (317) | H | 3-pyridyl | 2 | $n_D^{25.0}$ 1.5680 |
| (318) | H | 1-naphthyl | 2 | $n_D^{25.0}$ 1.6300 |
| (319) | H | 1-methylpyrrol-2-yl | 2 | $n_D^{26.0}$ 1.5661 |
| (320) | H | -C₆H₄-N(CH₃)₂ (para) | 2 | m.p. 78.7° C. |
| (321) | H | n-C₅H₁₁ | 2 | $n_D^{23.7}$ 1.4856 |
| (322) | H | —C(C₂H₅)=CHCH₃ | 2 | $n_D^{27.3}$ 1.5021 |
| (323) | H | cyclohexyl | 2 | $n_D^{27.0}$ 1.4990 |
| (324) | H | —CH₂CH₂—C₆H₅ | 2 | $n_D^{25.0}$ 1.5620 |
| (325) | H | —CH₂OCH₃ | 2 | $n_D^{25.0}$ 1.5029 |
| (326) | H | 3,4-dihydro-2H-pyran-2-yl | 2 | $n_D^{25.2}$ 1.5185 |
| (327) | H | 2-furyl | 2 | $n_D^{25.5}$ 1.5560 |
| (328) | H | —CH=CH—C₆H₅ | 2 | $n_D^{25.8}$ 1.6050 |
| (329) | H | -C₆H₄-SCH₃ (para) | 2 | $n_D^{24.4}$ 1.6121 |

TABLE 4-continued
Present compounds represented by the formula,
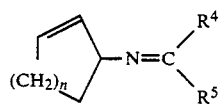
| Compound No. | R⁴ | R⁵ | n | Physical contant |
|---|---|---|---|---|
| (330) | H | 3-CF₃-C₆H₄- | 2 | $n_D^{24.0}$ 1.5116 |
| (331) | H | 3-Cl-2-OH-5-OC₂H₅-C₆H₂- | 2 | m.p. 140.3° C. |
| (332) | H | 3-(3-CF₃-C₆H₄-O)-C₆H₄- | 2 | $n_D^{25.3}$ 1.5110 |
| (333) | H | 4-OCH₃-2,3-(CH₃)₂-C₆H₂- | 2 | $n_D^{25.3}$ 1.5750 |
| (334) | H | 4-C₆H₅-C₆H₄- | 2 | m.p. 95.6° C. |
| (335) | H | 4-(C₆H₁₁-N=CH)-C₆H₄- | 2 | m.p. 97-100° C. |
| (336) | H | -CCl=CH-C₆H₅ | 2 | $n_D^{26.2}$ 1.6123 |
| (337) | H | 5-CH₃-thiophen-2-yl | 2 | $n_D^{24.5}$ 1.5858 |
| (338) | H | 3-(C₆H₅-CH₂-O)-C₆H₄- | 2 | $n_D^{25.2}$ 1.5945 |

TABLE 4-continued

Present compounds represented by the formula, $$\begin{array}{c} \diagup \hspace{-6pt}\diagdown \\ (CH_2)_n \end{array} \hspace{-4pt} \diagdown \hspace{-4pt} N=C \hspace{-4pt} \diagup \hspace{-4pt} \begin{array}{c} R^4 \\ R^5 \end{array}$$

| Compound No. | $R^4$ | $R^5$ | n | Physical contant |
|---|---|---|---|---|
| (339) | H | (4-ethylenedioxy-, 5-NO₂ phenyl) | 2 | $n_D^{25.1}$ 1.6070 |
| (340) | H | phenyl | 1 | $n_D^{24.0}$ 1.5686 |
| (341) | H | phenyl | 4 | $n_D^{25.2}$ 1.5600 |
| (342) | H | —C≡C—phenyl | 2 | $n_D^{27.5}$ 1.5911 |
| (343) | H | (2-Br, 3-OC₂H₅, 4-OC₂H₅ phenyl) | 2 | $n_D^{30.8}$ 1.5688 |
| (344) | —CH₂CH₂CH₂CH₂CH₂— | | 2 | C.A. 88, 49759k |

Method (1)

When the present compound is the salt of the amine compound represented by the foregoing formula (V), provided that when both $R^6$ and $R^7$ are a hydrogen atom, salts with the following acids are excluded for each value of n: when n is 1, hydrochloric acid, picric acid; when n is 2, hydrochloric acid, hydrobromic acid, phosphoric acid, methanesulfonic acid, ethanesulfonic acid, 2-hydroxyethanesulfonic acid, (2-cyclohexenylamino)methanesulfonic acid, (3-cyclohexenylamino)methanesulfonic acid, acetic acid, lactic acid, succinic acid, fumaric acid, maleic acid, malic acid, tartaric acid, citric acid, ascorbic acid, benzoic acid, salicylic acid, phenylacetic acid, mandelic acid, 4,4'-methylenebis(3-hydroxy-β-naphthoic acid); when n is 3, hydrochloric acid; and when n is 4, picric acid, the present compound can be produced by reacting an amine compound represented by the formula (V) with an acid of 0.95 to 1.0 equivalent based thereon at $-10°$ to 80° C. for preferably 0.5 to 1 hour.

The acid described above includes for example inorganic acids, organic acids (e.g. organic sulfonic acids, organic sulfinic acids, organic phosphoric acids, substituted or non-substituted aliphatic, aromatic or heteroaromatic carboxylic acids, substituted or non-substituted aliphatic polyhydric carboxylic acids or aromatic dicarboxylic acids, phenols and substituted or non-substituted dithiocarbamic acids, etc.), Lewis acids, etc.

More specifically, the inorganic acids include for example hydrochloric acid, hydrobromic acid, sulfuric acid, phosphoric acid, hydroiodic acid, hydrofluoric acid, sulfurous acid, nitric acid, nitrous acid, phosphorous acid, perchloric acid, chloric acid, chlorous acid, iodic acid, bromic acid, arsenic acid, carbonic acid, selenium hydride, tellurium hydride, phosphonic acid, hypophosphoric acid, diphosphonic acid, pyrophosphoric acid, metaphosphoric acid, polyphosphoric acid, selenic acid, selenious acid, telluric acid, tellurous acid, arsenious acid, antimonic acid, antimonous acid, borofluoric acid, etc. Of the organic acids, the organic sulfonic acids include for example hydroxymethanesulfonic acid, trifluoromethanesulfonic acid, β-bromoethanesulfonic acid, allylsulfonic acid, 2-methyl-2-[(1-oxo-2-propenyl)amino]-1-propanesulfonic acid, D-10-camphorsulfonic acid, benzenesulfonic acid, m-nitrobenzenesulfonic acid, m-benzenedisulfonic acid, methanesulfonic acid, ethanesulfonic acid, 2-hydroxyethanesulfonic acid, 2-(cyclohexenylamino)methanesulfonic acid, (3-cyclohexenylamino)methanesulfonic acid, p-ethylbenzenesulfonic acid, α-naphthalenesulfonic acid, β-naphthalenesulfonic acid, p-toluenesulfonic acid, p-chloromethylbenzenesulfonic acid, p-phenolsulfonic acid, 2-pyridylhydroxymethanesulfonic acid, 2,6-naphthalenedisulfonic acid, etc.; the organic sulfinic acids include for example benzenesulfinic acid, p-toluenesulfinic acid, etc.; the organic phosphoric acids include for example phenylphosphonous acid, butyphosphonous acid, methylphosphonous acid, dibenzenephosphinic acid, dibutylphosphinic acid, benzenephosphonic acid, methylphosphonic acid, phenylphosphinic acid, methylphosphinic acid, dibenzenethiophosphinic acid, dibutylthiophosphinic acid, benzenethiophosphonic acid, methylthiophosphonic acid, phenylthiophosphinic acid, methylthiophosphinic acid, benzenethiophosphonous acid, dibutylthiophosphonous acid, diethyl dithiophosphate, α-hydroxybenzylphosphonous acid, toluenephosphonous acid, etc.; the substituted or non-substituted aliphatic carboxylic acids include for example mandelic acid, acetic acid, lactic acid, ascorbic acid, phenylacetic acid, bromoacetic acid, trichloroacetic acid, chlorodifluoroacetic acid, thioacetic acid, glycolacetic acid, glyoxylic acid, acrylic acid, β-chloroacrylic acid, cyanoacetic acid, ethoxyacetic acid, β-chloropropionic acid, perfluoropropionic acid, propiolic acid, n-butyric acid, isobutyric acid, α-hydroxyisobutyric acid, crotonic acid, mucochloric acid, cyclopropanecarboxylic acid, isovaleric acid, 1-methylcyclopropanecarboxylic acid, 1-cyanocyclopropanecarboxylic acid, cyclobutanecarboxylic acid, cyclopentanecarboxylic acid, 2-ketobutyric acid, levulinic acid, pivalic acid, tert-butylacetic acid, coumarinic acid, 3-cyclohexenecarboxylic acid, β-2-furylacrylic acid, 3-pyridylacetic acid, phenylthioacetic acid, m-chlorophenylacetic acid, o-nitrophenylacetic acid, p-fluorophenylacetic acid, o-hydroxyphenylacetic acid, phenoxyacetic acid, o-chlorophenoxyacetic acid, 2,4-dichlorophenoxyacetic acid, 2,4,5-trichlorophenoxyacetic acid, cyclohexylacetic acid, 1-methyl-1-cyclohexanecarboxylic acid, 6-acetamidohexanoic acid, heptylic acid, dl-terebic acid, benzoylformic acid, cinnamic acid, o-chlorocinnamic acid, 2,4-dichlorocinnamic acid, m-nitrocinnamic acid, o-hydroxycinnamic acid, d -2-phenoxypropionic acid, 3-phenoxypropionic acid, 3-phenylpropionic acid, 3-(p-hydroxyphenyl)propionic acid, 2-(2,4,5-trichlorophenoxy)propionic acid, 4-methoxyphenylacetic acid, p-chloro-2-methylphenylacetic acid, 3,4-methylenedioxyphenylacetic acid, 4-chloro-2-methylphenoxyacetic acid, m-tolylacetic acid, α,α,α-trifluoro-m-tolylacetic acid, p-hydroxyphenylpyruvic acid, α-cyanocinnamic acid, p-methoxycinnamic acid, m-trifluoromethylcinnamic acid, 3,4-methylenedioxycinnamic acid 3,4-dimethoxyphenylacetic acid, (−)-α-methoxy-α-trifluoromethylphenylacetic acid, 1,4-benzdioxane-6-acetic acid, 3-phenyl-n-butyric acid, 1-phenyl-1-cyclopropanecarboxylic acid, 2-(p-hydroxyphenyl)-acetylene-1-carboxylic acid, 3-benzoylpropionic acid, 2-(p-chlorophenoxy)-2-methylpropionic acid, α-naphthylacetic acid, β-naphthoxyacetic acid, 3,4,5-trimethoxyphenylacetic acid, diphenylacetic acid, bis(p-chlorophenyl)acetic acid, l-menthoxyacetic acid, diphenyleneacetic acid, 1-phenylcyclopentanecarboxylic acid, 1-(p-chlorophenyl)-1-cyclopentanecarboxylic acid, dl-3-camphorcarboxylic acid, palmitic acid, stearic acid, benzilic acid, desoxycholic acid, linolic acid, oleic acid, α-acetamidocinnamic acid, etc.; the aromatic carboxylic acids include for example benzoic acid, salicylic acid, o-toluic acid, α,α,α-trifluoro-m-toluic acid, p-ethylbenzoic acid, 2,6-dimethylbenzoic acid, 2,4,6-trimethylbenzoic acid, p-tertbutylbenzoic acid, p-bromomethylbenzoic acid, 2-biphenylcarboxylic acid, 4,4'-methylenebis(3-hydroxy-β-naphthoic acid), α-naphthoic acid, p-benzoylbenzoic acid, phthalamic acid, o-phthalaldehydic acid, m-nitrobenzoic acid, 3,4-dinitrobenzoic acid, m-cyanobenzoic acid, thiosalicylic acid, gallic acid, m-hydroxybenzoic acid, 2,3-dihydroxybenzoic acid, 1-hydroxy-2-naphthoic acid, o-anisic acid, 3,4-dimethoxybenzoic acid, 4-hydroxy-3-methoxybenzoic acid, 4-hydroxy3,5-dimethoxybenzoic acid, 4-n-butoxybenzoic acid, 3-phenoxybenzoic acid, piperonylic acid, o-acetamidobenzoic acid, p-chlorobenzoic acid, 3,5-dichlorobenzoic acid, o-fluorobenzoic acid, m-fluorobenzoic acid, 2,6-difluorobenzoic acid, 2,6-dichlorobenzoic acid, 2,3,5-triiodobenzoic acid, 4-chlorosalicylic acid, 3-nitrosalicylic acid, 5-bromosalicylic acid, 2-chloro-3-nitrobenzoic acid, 3-chloro-4-hydroxybenzoic acid, 3,5-dichloro-4-hydroxybenzoic acid, 3-chloro-4-methylbenzoic acid, 3-methoxy-4-nitrobenzoic acid, 3-methoxy-4-hydroxybenzoic acid, 3-methoxy-4-methylbenzoic acid, 3-methyl-2-nitrobenzoic acid, 3-hydroxy-4-nitrobenzoic acid, 3,5-di-tert-butyl-4-hydroxybenzoic acid, o-thymotinic acid, etc.; the heteroaromatic carboxylic acids include for example N-methylpyrrole-2-carboxylic acid, 2-furancarboxylic acid, 5-bromo-2-furancarboxylic acid, pyrrole-2-carboxylic acid, 3-furancarboxylic acid, nicotinic acid, isonicotinic acid, citrazinic acid, α-picolinic acid, etc.; the substituted or non-substituted aliphatic polyhydric carboxylic acids include for example succinic acid, fumaric acid, maleic acid, malic acid, tartaric acid, citric acid, oxalic acid, malonic acid, ethylmalonic acid, hydroxymalonic acid, methylsuccinic acid, 2-methyl-2-phenylsuccinic acid, 2-ethyl-2-methylsuccinic acid; 2-isopropylsuccinic acid, bromosuccinic acid, 2,3-dibromosuccinic acid, α-ketoglutaric acid, 3-ethyl-3-methylglutaric acid, glutaconic acid, itaconic acid, mesaconic acid, citraconic acid, adipic acid, camphoric acid, diglycollic acid, acetylenedicarboxylic acid, dimethylcyclopropanedicarboxylic acid, etc.; the aromatic dicarboxylic acids include for example phthalic acid, isophthalic acid, terephthalic acid, homophthalic acid, 3-nitrophthalic acid, 4-hydroxyisophthalic acid, tetrachlorophthalic acid tetrachloroterephthalic acid, nitroterephthalic acid, pyrazine-2,3-dicarboxylic acid, o-phenylenediacetic acid, 5,5'-methylenedisalicylic acid, etc.; the phenols include for example picric acid, 2,4-dinitrophenol, 2,6-dinitrophenol, 2,6-diiodo-4-nitrophenol, 2,6-dichloro-4-nitrophenol, 2,5-dichloro-4-nitrophenol, 2,6-dibromo-4-nitrophenol, 2-bromo-4-chloro-6-nitrophenol, 2,4-dichloro-6-nitrophenol, etc.; and the substituted or non-substituted dithiocarbamic acids include for example 2-cyclohexenyldithiocarbamic acid, 2-cycloheptenyldithiocarbamic acid, methyldithiocarbamic acid, dimethyldithiocarbamic acid, ethylenebis(dithiocarbamic acid), etc. Further, the Lewis acid includes for example boron trifluoride, boron trichloride, boron tribromide, aluminum fluoride, aluminum chloride, aluminum bromide, aluminum iodide, aluminum sulfate, iron fluoride, iron chloride, iron bromide, iron nitrate, iron sulfate, gallium fluoride, gallium chloride, antimony fluoride, antimony chloride, antimony sulfate, indium fluoride, indium chloride, tin fluoride, tin chloride, tin bromide, tin iodide, arsenic fluoride, arsenic chloride, zinc fluoride, zinc chloride, zinc bromide, zinc iodide, copper chloride, barium chloride, silver chloride, etc.

The solvent used in the foregoing method includes for example aliphatic hydrocarbons such as hexane, heptane, ligroin, petroleum ether, etc., aromatic hydrocarbons such as benzene, toluene, xylene, etc., halogenated hydrocarbons such as chloroform, carbon tetrachloride, dichloroethane, chlorobenzene, dichlorobenzene, etc., ethers such as diethyl ether, diisopropyl ether, dioxane, tetrahydrofuran, diethylene glycol dimethyl ether, etc., ketones such as acetone, methyl ethyl ketone, methyl isobutyl ketone, isophorone, cyclohexanone, etc., alcohols such as methanol, ethanol, isopropanol, tert-butanol, octanol, cyclohexanol, methyl cellosolve, diethylene glycol, glycerin, etc., esters such as ethyl formate, ethyl acetate, butyl acetate, diethyl carbonate, etc., nitro compounds such as nitroethane, nitrobenzene, etc., nitriles such as acetonitrile, isobutyronitrile, etc., sulfur compounds such as dimethyl sulfoxide, sulfolane, etc., water, and mixtures thereof.

Next, examples of production of the present compound by the method (1) will be shown.

PRODUCTION EXAMPLE 17

Conc. hydrochloric acid (10.1 g) was added dropwise to a mixture of 2-cycloheptenylamine (11.1 g, 0.1 mole) and isopropyl alcohol (24 g) with stirring and ice-cooling. The reaction mixture was concentrated under reduced pressure, and the deposited crystal was washed with diethyl ether and dried to obtain 14 g of 2-cycloheptenylamine hydrochloride [Compound (349)].
m.p. 174°-176° C.

PRODUCTION EXAMPLE 18

To a solution of phenylphosphinic acid (0.72 g, 10 mmoles) in isopropyl alcohol (2.4 g) was added dropwise 2-cycloheptenylamine (0.56 g, 10 mmoles) with stirring and ice-cooling. The reaction mixture was concentrated under reduced pressure, and the deposited crystal was washed with diethyl ether and dried to obtain 1.2 g of the phenylphosphinic acid salt of 2-cycloheptenylamine [Compound (353)].
m.p. 171 -174° C.

Some of the present compounds which can be produced by this method are shown in Table 5 by means of corresponding acids.

TABLE 5

Salts of the 2-cycloalkenylamine derivative represented by the formula.

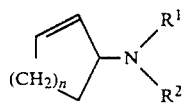

| Compound No. | R¹ | R² | n | Acid | Physical constant |
|---|---|---|---|---|---|
| (345) | H | CH₃ | 3 | Hydrochloric acid | m.p. 125° C. |
| (346) | H | H | 1 | — | C.A. 81,115149v |
| (347) | H | H | 3 | — | Ann. 317,243(1901) |
| (348) | H | H | 4 | — | C.A. 58,9005a |
| (349) | H | H | 3 | Hydrochloric acid | Ann. 317,243(1901) |
| (350) | H | H | 1 | Hydrochloric acid | C.A. 56,2341b |
| (351) | H | H | 4 | Hydrochloric acid | m.p. 271° C. |
| (352) | H | H | 1 | Picric acid | C.A. 56,2341b |
| (353) | H | H | 3 | Phenylphosphinic acid | m.p. 171-174° C. |
| (354) | H | H | 3 | Methylphosphinic acid | $n_D^{23.4}$ 1.4901 |
| (355) | H | H | 3 | α-Naphthalenesulfonic acid | $n_D^{23.4}$ 1.5581 |
| (356) | H | H | 3 | n-Butyric acid | $n_D^{23.4}$ 1.4827 |
| (357) | H | H | 3 | Zinc chloride | m.p. 137-144° C. |
| (358) | H | H | 3 | Ferric chloride | m.p. 137-140° C.(dec.) |
| (359) | H | H | 3 | p-Toluenesulfinic acid | m.p. 156-159° C. |
| (360) | H | H | 3 | 3-Chloropropionic acid | m.p. 82-85° C. |
| (361) | H | H | 3 | Benzoic acid | m.p. 167-170° C. |
| (362) | H | H | 3 | o-Anisic acid | m.p. 160-163° C. |
| (363) | H | H | 3 | 2-Furancarboxylic acid | m.p. 187-190° C. |
| (364) | H | H | 3 | Maleic acid | m.p. 100-103° C. |
| (365) | H | H | 3 | Phthalic acid | m.p. 151-154° C. |
| (366) | H | H | 1 | 2,4-Dinitrophenol | m.p. 164-166° C. |
| (367) | H | H | 3 | Acetic acid | m.p. 86° C. |
| (368) | H | H | 3 | $CH_3CH-\overset{\overset{O}{\|}}{\underset{OH}{P}}-\overset{}{\underset{H}{OH}}$ | $n_D^{18.4}$ 1.5076 |
| (369) | H | —CH(CH₃)CN | 3 | Phenylphosphinic acid | m.p. 95° C. |
| (370) | H | —CH(CH₃)CN | 3 | Methylphosphinic acid | $n_D^{22.0}$ 1.5000 |
| (371) | H | —CH₂CN | 3 | Phenylphosphinic acid | m.p. 77° C. |
| (372) | CH₃ | CH₃ | 3 | Hydrochloric acid | m.p. 159° C. |
| (373) | CH₃ | CH₃ | 3 | Phenylphosphinic acid | $n_D^{23.6}$ 1.5389 |
| (374) | CH₃ | H | 3 | Phenylphosphinic acid | $n_D^{23.5}$ 1.5400 |

When the present compounds thus obtained are used as the active ingredient of soil disease-controllnig agents, they may be used as such without adding any other components, but generally, they are formulated into emulsifiable concentrates, wettable powders, suspension formulations, granules, dusts, water-soluble formulations, fine granules and the like by mixing with solid carriers, liquid carriers, surface active agents and other auxiliaries for formulation.

These formulations contain the present compound as an active ingredient in amounts of 0.1 to 99.9%, preferably 0.2 to 80.0% by weight ratio.

The above solid carrier includes for example the fine powders or granules of kaolin clay, attapulgite clay, bentonite, terra abla, pyrophyllite, talc, diatomaceous earth, calcite, corn stalk powder, walnut shell powder, urea, ammonium sulfate, synthetic hydrated silicon dioxide, etc. The liquid carrier includes for example aromatic hydrocarbons (e.g. xylene, methylnaphthalene), alcohols (e.g. isopropanol, ethylene glycol, cellosolve), ketones (e.g. acetone, cyclohexanone, isophorone), vegetable oils (e.g. soybean oil, cotton seed oil), dimethyl sulfoxide, acetonitrile, water and the like.

As the surface active agent used for emulsification, dispersion, wetting, etc., there are given for examples anionic surface active agents such as the salt of alkyl sulfate, alkyl(aryl) sulfonates, dialkyl sulfosuccinates, the salt of the phosphoric acid ester of polyoxyethylene alkylaryl ether, naphthalenesulfonic acid/formalin condensates, etc. and nonionic surface active agents such as polyoxyethylene alkyl ether, polyoxyethylene polyoxypropylene block copolymers, sorbitan fatty acid esters, polyoxyethylene sorbitan fatty acid esters, etc. The auxiliary for formulation includes for example lignosulfonates, alginates, polyvinyl alcohol, gum arabic, CMC (carboxymethyl cellulose), PAP (isopropyl acid phosphate) and the like.

Next, formulation examples will be shown. The present compounds are shown by Compound No. in Tables 1 to 5. Parts in the examples are by weight.

FORMULATION EXAMPLE 1

Two parts of the compound (2), 88 parts of kaolin clay and 10 parts of talc are thoroughly mixed while being powdered to obtain a dust.

FORMULATION EXAMPLE 2

Two parts of the compound (4), 1 part of synthetic hydrated silicon dioxide, 2 parts of calcium lignosulfonate, 30 parts of bentonite and 65 parts of kaolin clay are thoroughly mixed while being powdered, well kneaded with water, granulated and then dried to obtain a granule.

FORMULATION EXAMPLE 3

Fifty parts of the compound (123), 3 parts of calcium lignosulfonate, 2 parts of sodium lauryl sulfate and 45 parts of synthetic hydrated silicon dioxide are thoroughly mixed while being powdered to obtain a wettable powder.

FORMULATION EXAMPLE 4

Ten parts of the compound (217), 14 parts of polyoxyethylene styrylphenyl ether, 6 parts of calcium dodecylbenzenesulfonate, 30 parts of xylene and 40 parts of isopropanol are thoroughly mixed to obtain an emulsifiable concentrate.

FORMULATION EXAMPLE 5

Thirty parts of the compound (280) is dissolved in dimethyl sulfoxide, and the resulting solution is adsorbed in 70 parts of attapulgite clay. The clay impregnated with the solution is then dried to obtain a fine granule.

FORMULATION EXAMPLE 6

Ten parts of the compound (349), 1 part of polyoxyethylene styrylphenyl ether and 89 parts of water are mixed to obtain a water-soluble formulation.

These formulations, either are such or as aqueous dilute liquors, are used in foliar treatment or soil treatment. In the case of soil treatment, the formulations are sprayed (or scattered) onto soil surface [as need arises, they are mixed with the soil after spraying (or scattering)], or the soil is drenched with them. Also, an increase in the controlling effect can be expected by using them in mixtuer with other soil disease-controlling agents. Further, these formulations may also be used in mixture with other fungicides, soil insect pest controlling agents, nematocides, plant growth regulating agents, fertilizers, soil improvers and the like.

When the present compound is used as the active ingredient of soil disease controllng agents, its dosage rate is generally 0.001 to 50 kg per 10 ares, preferably 0.01 to 10 kg per 10 ares. The granule, dust, fine granule, etc. are used as such without dilution, and when the emulsifiable concentrate, wettable powder, suspension formulation, water-soluble formulation, etc. are used as aqueous dilute liquors, their application concentration is 0.0005 to to 5.0%, preferably 0.005 to 0.5%.

Next, that the present compound is useful as the active ingredient of soil disease controlnig agents will be illustrated with reference to the following test examples. Hereupon, the present compounds are shown by Compound No. in Tables 1 to 5, and compounds used as a control are shown by Compound symbol in Table 6.

TABLE 6

| Compound symbol | Chemical structure | Remark |
|---|---|---|
| A | (benzimidazole with CONHC$_4$H$_{9-n}$ and NHCOOCH$_3$ substituents) | Benomyl (commercial fungicide) |
| B | CCl$_3$NO$_2$ | Chloropicrin (commercial fumigant) |
| C | (isoxazole with OH, H$_3$C substituents) | Hydroxyisoxazole (commerical fungicide) |
| D | (pentachloronitrobenzene: Cl$_5$C$_6$NO$_2$) | PCNB (commercial fungicide) |

The controlling effect is indicated by thenumerical value of the percentage of healthy seedlings obtained as follows: The condition of disease of test plants on examination, i.e. the degrees of the colony and symptom on the leaves, stems, roots, etc. of the test plants are observed with the naked eye; the number of test plants showing no colony nor symptom at all (hereinafter referred to as number of healthy seedlings) is counted for each case described below: A case wherein the compound was applied (hereinafter referred to as number of healthy seedlings in treated plot) and another case wherein neither application of the compound nor inoculatoin of pathogens was carried out (hereinafter referred to as number of healthy seedlings in untreated and uninoculated plot); and the percentage of healthy seedlings (%) is obtained from the following equation:

$$\text{Percentage of healthy seedlings (\%)} = \frac{\text{Number of healthy seedlings in treated plot}}{\text{Number of healthy seedlings in untreated and uninoculated plot}} \times 100$$

TEST EXAMPLE 1

Controlling Effect Against Yellows of Japanese Radish (*Fusarium oxysporum* f.sp. *raphani*)

A plastic pot was filled with a well mixed soil of field soil and infested soil containing cultured *Fusarium oxysporum* f.sp. *raphani*, and the seed of radish (variety, Wase-40 nichi) was sowed at a rate of 15/pot and covered with soil. Thereafter, a prescribed amount of each test compound in the form of wettable powder-formulated according to Formulation example 3 was diluted with water and applied to soil drenching. After three weeks' cultivation in a greenhouse, the controlling effect was examined.

The results are shown in Table 7.

TABLE 7

| Test compound | Dosage rate of active ingredient (g/10 are) | Percentage of healthy seedlings (%) | Phytotoxicity |
|---|---|---|---|
| (1) | 300 | 100.0 | — |
| (2) | " | 100.0 | — |
| (3) | " | 100.0 | — |
| (4) | " | 100.0 | — |
| (5) | " | 100.0 | — |
| (6) | " | 100.0 | — |
| (7) | " | 100.0 | — |
| (8) | " | 100.0 | — |
| (9) | " | 100.0 | — |
| (10) | " | 100.0 | — |
| (11) | " | 100.0 | — |
| (12) | " | 100.0 | — |
| (13) | " | 100.0 | — |
| (14) | " | 100.0 | — |
| (15) | " | 100.0 | — |
| (16) | " | 100.0 | — |
| (17) | " | 100.0 | — |
| (18) | " | 100.0 | — |
| (19) | " | 100.0 | — |
| (20) | " | 100.0 | — |
| (21) | " | 100.0 | — |
| (22) | " | 100.0 | — |
| (23) | " | 100.0 | — |
| (24) | " | 100.0 | — |
| (25) | " | 100.0 | — |
| (26) | " | 100.0 | — |
| (27) | " | 100.0 | — |
| (28) | " | 100.0 | — |
| (29) | " | 100.0 | — |
| (30) | " | 100.0 | — |
| (31) | " | 100.0 | — |
| (32) | " | 100.0 | — |
| (33) | " | 100.0 | — |
| (34) | " | 100.0 | — |
| (35) | " | 100.0 | — |
| (36) | " | 100.0 | — |
| (37) | " | 100.0 | — |
| (38) | " | 100.0 | — |
| (39) | " | 100.0 | — |
| (40) | " | 100.0 | — |
| (41) | " | 100.0 | — |
| (42) | " | 100.0 | — |
| (43) | " | 100.0 | — |
| (44) | " | 100.0 | — |
| (45) | " | 100.0 | — |
| (46) | " | 100.0 | — |
| (47) | " | 100.0 | — |
| (48) | " | 100.0 | — |
| (49) | " | 100.0 | — |
| (50) | " | 100.0 | — |
| (51) | " | 100.0 | — |
| (52) | " | 100.0 | — |
| (53) | " | 100.0 | — |
| (54) | " | 100.0 | — |
| (55) | " | 100.0 | — |
| (56) | " | 100.0 | — |
| (57) | " | 100.0 | — |
| (58) | " | 100.0 | — |
| (59) | " | 100.0 | — |
| (60) | " | 100.0 | — |
| (61) | " | 100.0 | — |
| (62) | " | 100.0 | — |
| (63) | " | 100.0 | — |
| (64) | " | 100.0 | — |
| (65) | " | 100.0 | — |
| (66) | " | 100.0 | — |
| (67) | " | 100.0 | — |
| (68) | " | 100.0 | — |
| (69) | " | 100.0 | — |
| (70) | " | 100.0 | — |
| (71) | " | 100.0 | — |
| (72) | " | 100.0 | — |
| (73) | " | 100.0 | — |
| (74) | " | 100.0 | — |
| (75) | " | 100.0 | — |
| (76) | " | 100.0 | — |
| (77) | " | 100.0 | — |
| (78) | " | 100.0 | — |
| (79) | " | 100.0 | — |
| (80) | " | 100.0 | — |
| (81) | " | 100.0 | — |
| (82) | " | 100.0 | — |
| (83) | " | 100.0 | — |
| (84) | " | 100.0 | — |
| (85) | " | 100.0 | — |
| (86) | " | 100.0 | — |
| (87) | " | 100.0 | — |
| (88) | " | 100.0 | — |
| (89) | " | 100.0 | — |
| (90) | " | 100.0 | — |
| (91) | " | 100.0 | — |
| (92) | " | 100.0 | — |
| (93) | " | 100.0 | — |
| (94) | " | 100.0 | — |
| (95) | " | 100.0 | — |
| (96) | " | 100.0 | — |
| (97) | " | 100.0 | — |
| (98) | " | 100.0 | — |
| (99) | " | 100.0 | — |
| (100) | " | 100.0 | — |
| (101) | " | 100.0 | — |
| (102) | " | 100.0 | — |
| (103) | " | 100.0 | — |
| (104) | " | 100.0 | — |
| (105) | " | 100.0 | — |
| (106) | " | 100.0 | — |
| (107) | " | 100.0 | — |
| (108) | " | 100.0 | — |
| (109) | " | 100.0 | — |
| (110) | " | 100.0 | — |
| (111) | " | 100.0 | — |
| (112) | " | 100.0 | — |
| (113) | " | 100.0 | — |
| (114) | " | 100.0 | — |
| (115) | " | 100.0 | — |
| (116) | " | 100.0 | — |
| (117) | " | 100.0 | — |
| (118) | " | 100.0 | — |
| (119) | " | 100.0 | — |
| (120) | " | 100.0 | — |
| (121) | " | 100.0 | — |
| (122) | " | 100.0 | — |
| (123) | " | 100.0 | — |
| (124) | " | 100.0 | — |
| (125) | " | 100.0 | — |
| (126) | " | 100.0 | — |
| (127) | " | 100.0 | — |
| (128) | " | 100.0 | — |
| (129) | " | 100.0 | — |
| (130) | " | 100.0 | — |
| (131) | " | 100.0 | — |
| (132) | " | 100.0 | — |
| (133) | " | 100.0 | — |
| (134) | " | 100.0 | — |
| (135) | " | 100.0 | — |
| (136) | " | 100.0 | — |
| (137) | " | 100.0 | — |
| (138) | " | 100.0 | — |

TABLE 7-continued

| Test compound | Dosage rate of active ingredient (g/10 are) | Percentage of healthy seedlings (%) | Phytotoxicity |
|---|---|---|---|
| (139) | " | 100.0 | — |
| (140) | " | 100.0 | — |
| (141) | " | 100.0 | — |
| (142) | " | 100.0 | — |
| (143) | " | 100.0 | — |
| (144) | " | 100.0 | — |
| (145) | " | 100.0 | — |
| (146) | " | 100.0 | — |
| (147) | " | 100.0 | — |
| (148) | " | 100.0 | — |
| (149) | " | 100.0 | — |
| (150) | " | 100.0 | — |
| (151) | " | 100.0 | — |
| (152) | " | 100.0 | — |
| (153) | " | 100.0 | — |
| (154) | " | 100.0 | — |
| (155) | " | 100.0 | — |
| (156) | " | 100.0 | — |
| (157) | " | 100.0 | — |
| (158) | " | 100.0 | — |
| (159) | " | 100.0 | — |
| (160) | " | 100.0 | — |
| (161) | " | 100.0 | — |
| (162) | " | 100.0 | — |
| (163) | " | 100.0 | — |
| (164) | " | 100.0 | — |
| (165) | " | 100.0 | — |
| (166) | " | 100.0 | — |
| (167) | " | 100.0 | — |
| (168) | " | 100.0 | — |
| (169) | " | 100.0 | — |
| (170) | " | 100.0 | — |
| (171) | " | 100.0 | — |
| (172) | " | 100.0 | — |
| (173) | " | 100.0 | — |
| (174) | " | 100.0 | — |
| (175) | " | 100.0 | — |
| (176) | " | 100.0 | — |
| (177) | " | 100.0 | — |
| (178) | " | 100.0 | — |
| (179) | " | 100.0 | — |
| (180) | " | 100.0 | — |
| (181) | " | 100.0 | — |
| (182) | " | 100.0 | — |
| (183) | " | 100.0 | — |
| (184) | " | 100.0 | — |
| (185) | " | 100.0 | — |
| (186) | " | 100.0 | — |
| (187) | " | 100.0 | — |
| (188) | " | 100.0 | — |
| (189) | " | 100.0 | — |
| (190) | " | 100.0 | — |
| (191) | " | 100.0 | — |
| (192) | " | 100.0 | — |
| (193) | " | 100.0 | — |
| (194) | " | 100.0 | — |
| (195) | " | 100.0 | — |
| (196) | " | 100.0 | — |
| (197) | " | 100.0 | — |
| (198) | " | 100.0 | — |
| (199) | " | 100.0 | — |
| (200) | " | 100.0 | — |
| (201) | " | 100.0 | — |
| (202) | " | 100.0 | — |
| (203) | " | 100.0 | — |
| (204) | " | 100.0 | — |
| (205) | " | 100.0 | — |
| (206) | " | 100.0 | — |
| (207) | " | 100.0 | — |
| (208) | " | 100.0 | — |
| (209) | " | 100.0 | — |
| (210) | " | 100.0 | — |
| (211) | " | 100.0 | — |
| (212) | " | 100.0 | — |
| (213) | " | 100.0 | — |
| (214) | " | 100.0 | — |
| (215) | " | 100.0 | — |
| (216) | " | 100.0 | — |
| (217) | " | 100.0 | — |
| (218) | " | 100.0 | — |
| (219) | " | 100.0 | — |
| (220) | " | 100.0 | — |
| (221) | " | 100.0 | — |
| (222) | " | 100.0 | — |
| (223) | " | 100.0 | — |
| (224) | " | 100.0 | — |
| (225) | " | 100.0 | — |
| (226) | " | 100.0 | — |
| (227) | " | 100.0 | — |
| (228) | " | 100.0 | — |
| (229) | " | 100.0 | — |
| (230) | " | 100.0 | — |
| (231) | " | 100.0 | — |
| (232) | " | 100.0 | — |
| (233) | " | 100.0 | — |
| (234) | " | 100.0 | — |
| (235) | " | 100.0 | — |
| (236) | " | 100.0 | — |
| (237) | " | 100.0 | — |
| (238) | " | 100.0 | — |
| (239) | " | 100.0 | — |
| (240) | " | 100.0 | — |
| (241) | " | 100.0 | — |
| (242) | " | 100.0 | — |
| (243) | " | 100.0 | — |
| (244) | " | 100.0 | — |
| (245) | " | 100.0 | — |
| (246) | " | 100.0 | — |
| (247) | " | 100.0 | — |
| (248) | " | 100.0 | — |
| (249) | " | 100.0 | — |
| (250) | " | 100.0 | — |
| (251) | " | 100.0 | — |
| (252) | " | 100.0 | — |
| (253) | " | 100.0 | — |
| (254) | " | 100.0 | — |
| (255) | " | 100.0 | — |
| (256) | " | 100.0 | — |
| (257) | " | 100.0 | — |
| (258) | " | 100.0 | — |
| (259) | " | 100.0 | — |
| (260) | " | 100.0 | — |
| (261) | " | 100.0 | — |
| (262) | " | 100.0 | — |
| (263) | " | 100.0 | — |
| (264) | " | 100.0 | — |
| (265) | " | 100.0 | — |
| (266) | " | 100.0 | — |
| (267) | " | 100.0 | — |
| (268) | " | 100.0 | — |
| (269) | " | 100.0 | — |
| (270) | " | 100.0 | — |
| (271) | " | 100.0 | — |
| (272) | " | 100.0 | — |
| (273) | " | 100.0 | — |
| (274) | " | 100.0 | — |
| (275) | " | 100.0 | — |
| (276) | " | 100.0 | — |
| (277) | " | 100.0 | — |
| (278) | " | 100.0 | — |
| (279) | " | 100.0 | — |
| (280) | " | 100.0 | — |
| (281) | " | 100.0 | — |
| (282) | " | 100.0 | — |
| (283) | " | 100.0 | — |
| (284) | " | 100.0 | — |
| (285) | " | 100.0 | — |
| (286) | " | 100.0 | — |
| (287) | " | 100.0 | — |
| (288) | " | 100.0 | — |
| (289) | " | 100.0 | — |
| (290) | " | 100.0 | — |
| (291) | " | 100.0 | — |
| (292) | " | 100.0 | — |
| (293) | " | 100.0 | — |
| (294) | " | 100.0 | — |
| (295) | " | 100.0 | — |
| (296) | " | 100.0 | — |

TABLE 7-continued

| Test compound | Dosage rate of active ingredient (g/10 are) | Percentage of healthy seedlings (%) | Phytotoxicity |
|---|---|---|---|
| (297) | " | 100.0 | — |
| (298) | " | 100.0 | — |
| (299) | " | 100.0 | — |
| (300) | " | 100.0 | — |
| (301) | " | 100.0 | — |
| (302) | " | 100.0 | — |
| (303) | " | 100.0 | — |
| (304) | " | 100.0 | — |
| (305) | " | 100.0 | — |
| (306) | " | 100.0 | — |
| (307) | " | 100.0 | — |
| (308) | " | 100.0 | — |
| (309) | " | 100.0 | — |
| (310) | " | 100.0 | — |
| (311) | " | 100.0 | — |
| (312) | " | 100.0 | — |
| (313) | " | 100.0 | — |
| (314) | " | 100.0 | — |
| (315) | " | 100.0 | — |
| (316) | " | 100.0 | — |
| (317) | " | 100.0 | — |
| (318) | " | 100.0 | — |
| (319) | " | 100.0 | — |
| (320) | " | 100.0 | — |
| (321) | " | 100.0 | — |
| (322) | " | 100.0 | — |
| (323) | " | 100.0 | — |
| (324) | " | 100.0 | — |
| (325) | " | 100.0 | — |
| (326) | " | 100.0 | — |
| (327) | " | 100.0 | — |
| (328) | " | 100.0 | — |
| (329) | " | 100.0 | — |
| (330) | " | 100.0 | — |
| (331) | " | 100.0 | — |
| (332) | " | 100.0 | — |
| (333) | " | 100.0 | — |
| (334) | " | 100.0 | — |
| (335) | " | 100.0 | — |
| (336) | " | 100.0 | — |
| (337) | " | 100.0 | — |
| (338) | " | 100.0 | — |
| (339) | " | 100.0 | — |
| (340) | " | 100.0 | — |
| (341) | " | 100.0 | — |
| (342) | " | 100.0 | — |
| (343) | " | 100.0 | — |
| (344) | " | 100.0 | — |
| (345) | " | 100.0 | — |
| (346) | " | 100.0 | — |
| (347) | " | 100.0 | — |
| (348) | " | 100.0 | — |
| (349) | " | 100.0 | — |
| (350) | " | 100.0 | — |
| (351) | " | 100.0 | — |
| (352) | " | 100.0 | — |
| (353) | " | 100.0 | — |
| (354) | " | 100.0 | — |
| (355) | " | 100.0 | — |
| (356) | " | 100.0 | — |
| (357) | " | 100.0 | — |
| (358) | " | 100.0 | — |
| (359) | " | 100.0 | — |
| (360) | " | 100.0 | — |
| (361) | " | 100.0 | — |
| (362) | " | 100.0 | — |
| (363) | " | 100.0 | — |
| (364) | " | 100.0 | — |
| (365) | " | 100.0 | — |
| (366) | " | 100.0 | — |
| (367) | " | 100.0 | — |
| (368) | " | 100.0 | — |
| (369) | " | 100.0 | — |
| (370) | " | 100.0 | — |
| (371) | " | 100.0 | — |
| (372) | " | 100.0 | — |
| (373) | " | 100.0 | — |
| (374) | " | 100.0 | — |
| A | 600 | 57.8 | — |
| Inoculated and untreated plot | — | 8.9 | — |
| Uninoculated and untreated plot | — | 100.0 | — |

TEST EXAMPLE 2

Controlling Effect Against Yellows of Cabbage (*Fusarium oxysporum* f.sp. *conglutinans*)

A plastic pot was filled with a uniform mixture of field soil, infested soil containin cultured *Fusarium oxysporum* f.sp. *conglutinans* and a prescribed amount of each test compound in the form of fine granule formulated according to Formulation example 5. In this test, chlorpicrin was used as follows: After the field soil and infested soil were well mixed and filled in the plastic pot, a prescribed amount of chloropicrin was injected into the soil which was then covered with a polyvinyl chloride film and allowed to stand for one week; thereafter the film was removed and gas release was carried out for one week. The seed of cabbage (variety, Shikidori) was sowed at a rate of 10/pot and covered with soil. After three weeks' cultivation in a greenhouse, the controlling effect was examined.

The results are shown in Table 8.

TABLE 8

| Test compound | Dosage rate of active ingredient (g/10 are) | Percentage of healthy seedlings (%) | Phytotoxicity |
|---|---|---|---|
| (1) | 300 | 100.0 | — |
| (2) | 300 | 100.0 | — |
| (3) | 300 | 100.0 | — |
| (4) | 300 | 100.0 | — |
| (5) | 300 | 100.0 | — |
| (6) | 300 | 100.0 | — |
| (7) | 300 | 100.0 | — |
| (8) | 300 | 100.0 | — |
| (9) | 300 | 100.0 | — |
| (10) | 300 | 100.0 | — |
| (11) | 300 | 100.0 | — |
| (12) | 300 | 100.0 | — |
| (13) | 300 | 100.0 | — |
| (14) | 300 | 100.0 | — |
| (15) | 300 | 100.0 | — |
| (16) | 300 | 100.0 | — |
| (17) | 300 | 100.0 | — |
| (18) | 300 | 100.0 | — |
| (19) | 300 | 100.0 | — |
| (20) | 300 | 100.0 | — |
| (21) | 300 | 100.0 | — |
| (22) | 300 | 100.0 | — |
| (23) | 300 | 100.0 | — |
| (24) | 300 | 100.0 | — |
| (25) | 300 | 100.0 | — |
| (26) | 300 | 100.0 | — |
| (27) | 300 | 100.0 | — |
| (28) | 300 | 100.0 | — |
| (29) | 300 | 100.0 | — |
| (30) | 300 | 100.0 | — |
| (31) | 300 | 100.0 | — |
| (32) | 300 | 100.0 | — |
| (33) | 300 | 100.0 | — |
| (34) | 300 | 100.0 | — |
| (35) | 300 | 100.0 | — |
| (36) | 300 | 100.0 | — |
| (37) | 300 | 100.0 | — |
| (38) | 300 | 100.0 | — |
| (39) | 300 | 100.0 | — |
| (40) | 300 | 100.0 | — |
| (41) | 300 | 100.0 | — |
| (42) | 300 | 100.0 | — |

TABLE 8-continued

| Test compound | Dosage rate of active ingredient (g/10 are) | Percentage of healthy seedlings (%) | Phytotoxicity |
|---|---|---|---|
| (43) | 300 | 100.0 | — |
| (44) | 300 | 100.0 | — |
| (45) | 300 | 100.0 | — |
| (46) | 300 | 100.0 | — |
| (47) | 300 | 100.0 | — |
| (48) | 300 | 100.0 | — |
| (49) | 300 | 100.0 | — |
| (50) | 300 | 100.0 | — |
| (51) | 300 | 100.0 | — |
| (52) | 300 | 100.0 | — |
| (53) | 300 | 100.0 | — |
| (54) | 300 | 100.0 | — |
| (55) | 300 | 100.0 | — |
| (56) | 300 | 100.0 | — |
| (57) | 300 | 100.0 | — |
| (58) | 300 | 100.0 | — |
| (59) | 300 | 100.0 | — |
| (60) | 300 | 100.0 | — |
| (61) | 300 | 100.0 | — |
| (62) | 300 | 100.0 | — |
| (63) | 300 | 100.0 | — |
| (64) | 300 | 100.0 | — |
| (65) | 300 | 100.0 | — |
| (66) | 300 | 100.0 | — |
| (67) | 300 | 100.0 | — |
| (68) | 300 | 100.0 | — |
| (69) | 300 | 100.0 | — |
| (70) | 300 | 100.0 | — |
| (71) | 300 | 100.0 | — |
| (72) | 300 | 100.0 | — |
| (73) | 300 | 100.0 | — |
| (74) | 300 | 100.0 | — |
| (75) | 300 | 100.0 | — |
| (76) | 300 | 100.0 | — |
| (77) | 300 | 100.0 | — |
| (78) | 300 | 100.0 | — |
| (79) | 300 | 100.0 | — |
| (80) | 300 | 100.0 | — |
| (81) | 300 | 100.0 | — |
| (82) | 300 | 100.0 | — |
| (83) | 300 | 100.0 | — |
| (84) | 300 | 100.0 | — |
| (85) | 300 | 100.0 | — |
| (86) | 300 | 100.0 | — |
| (87) | 300 | 100.0 | — |
| (88) | 300 | 100.0 | — |
| (89) | 300 | 100.0 | — |
| (90) | 300 | 100.0 | — |
| (91) | 300 | 100.0 | — |
| (92) | 300 | 100.0 | — |
| (93) | 300 | 100.0 | — |
| (94) | 300 | 100.0 | — |
| (95) | 300 | 100.0 | — |
| (96) | 300 | 100.0 | — |
| (97) | 300 | 100.0 | — |
| (98) | 300 | 100.0 | — |
| (99) | 300 | 100.0 | — |
| (100) | 300 | 100.0 | — |
| (101) | 300 | 100.0 | — |
| (102) | 300 | 100.0 | — |
| (103) | 300 | 100.0 | — |
| (104) | 300 | 100.0 | — |
| (105) | 300 | 100.0 | — |
| (106) | 300 | 100.0 | — |
| (107) | 300 | 100.0 | — |
| (108) | 300 | 100.0 | — |
| (109) | 300 | 100.0 | — |
| (110) | 300 | 100.0 | — |
| (111) | 300 | 100.0 | — |
| (112) | 300 | 100.0 | — |
| (113) | 300 | 100.0 | — |
| (114) | 300 | 100.0 | — |
| (115) | 300 | 100.0 | — |
| (116) | 300 | 100.0 | — |
| (117) | 300 | 100.0 | — |
| (118) | 300 | 100.0 | — |
| (119) | 300 | 100.0 | — |
| (120) | 300 | 100.0 | — |
| (121) | 300 | 100.0 | — |
| (122) | 300 | 100.0 | — |
| (123) | 300 | 100.0 | — |
| (124) | 300 | 100.0 | — |
| (125) | 300 | 100.0 | — |
| (126) | 300 | 100.0 | — |
| (127) | 300 | 100.0 | — |
| (128) | 300 | 100.0 | — |
| (129) | 300 | 100.0 | — |
| (130) | 300 | 100.0 | — |
| (131) | 300 | 100.0 | — |
| (132) | 300 | 100.0 | — |
| (133) | 300 | 100.0 | — |
| (134) | 300 | 100.0 | — |
| (135) | 300 | 100.0 | — |
| (136) | 300 | 100.0 | — |
| (137) | 300 | 100.0 | — |
| (138) | 300 | 100.0 | — |
| (139) | 300 | 100.0 | — |
| (140) | 300 | 100.0 | — |
| (141) | 300 | 100.0 | — |
| (142) | 300 | 100.0 | — |
| (143) | 300 | 100.0 | — |
| (144) | 300 | 100.0 | — |
| (145) | 300 | 100.0 | — |
| (146) | 300 | 100.0 | — |
| (147) | 300 | 100.0 | — |
| (148) | 300 | 100.0 | — |
| (149) | 300 | 100.0 | — |
| (150) | 300 | 100.0 | — |
| (151) | 300 | 100.0 | — |
| (152) | 300 | 100.0 | — |
| (153) | 300 | 100.0 | — |
| (154) | 300 | 100.0 | — |
| (155) | 300 | 100.0 | — |
| (156) | 300 | 100.0 | — |
| (157) | 300 | 100.0 | — |
| (158) | 300 | 100.0 | — |
| (159) | 300 | 100.0 | — |
| (160) | 300 | 100.0 | — |
| (161) | 300 | 100.0 | — |
| (162) | 300 | 100.0 | — |
| (163) | 300 | 100.0 | — |
| (164) | 300 | 100.0 | — |
| (165) | 300 | 100.0 | — |
| (166) | 300 | 100.0 | — |
| (167) | 300 | 100.0 | — |
| (168) | 300 | 100.0 | — |
| (169) | 300 | 100.0 | — |
| (170) | 300 | 100.0 | — |
| (171) | 300 | 100.0 | — |
| (172) | 300 | 100.0 | — |
| (173) | 300 | 100.0 | — |
| (174) | 300 | 100.0 | — |
| (175) | 300 | 100.0 | — |
| (176) | 300 | 100.0 | — |
| (177) | 300 | 100.0 | — |
| (178) | 300 | 100.0 | — |
| (179) | 300 | 100.0 | — |
| (180) | 300 | 100.0 | — |
| (181) | 300 | 100.0 | — |
| (182) | 300 | 100.0 | — |
| (183) | 300 | 100.0 | — |
| (184) | 300 | 100.0 | — |
| (185) | 300 | 100.0 | — |
| (186) | 300 | 100.0 | — |
| (187) | 300 | 100.0 | — |
| (188) | 300 | 100.0 | — |
| (189) | 300 | 100.0 | — |
| (190) | 300 | 100.0 | — |
| (191) | 300 | 100.0 | — |
| (192) | 300 | 100.0 | — |
| (193) | 300 | 100.0 | — |
| (194) | 300 | 100.0 | — |
| (195) | 300 | 100.0 | — |
| (196) | 300 | 100.0 | — |
| (197) | 300 | 100.0 | — |
| (198) | 300 | 100.0 | — |
| (199) | 300 | 100.0 | — |
| (200) | 300 | 100.0 | — |

TABLE 8-continued

| Test compound | Dosage rate of active ingredient (g/10 are) | Percentage of healthy seedlings (%) | Phytotoxicity |
|---|---|---|---|
| (201) | 300 | 100.0 | — |
| (202) | 300 | 100.0 | — |
| (203) | 300 | 100.0 | — |
| (204) | 300 | 100.0 | — |
| (205) | 300 | 100.0 | — |
| (206) | 300 | 100.0 | — |
| (207) | 300 | 100.0 | — |
| (208) | 300 | 100.0 | — |
| (209) | 300 | 100.0 | — |
| (210) | 300 | 100.0 | — |
| (211) | 300 | 100.0 | — |
| (212) | 300 | 100.0 | — |
| (213) | 300 | 100.0 | — |
| (214) | 300 | 100.0 | — |
| (215) | 300 | 100.0 | — |
| (216) | 300 | 100.0 | — |
| (217) | 300 | 100.0 | — |
| (218) | 300 | 100.0 | — |
| (219) | 300 | 100.0 | — |
| (220) | 300 | 100.0 | — |
| (221) | 300 | 100.0 | — |
| (222) | 300 | 100.0 | — |
| (223) | 300 | 100.0 | — |
| (224) | 300 | 100.0 | — |
| (225) | 300 | 100.0 | — |
| (226) | 300 | 100.0 | — |
| (227) | 300 | 100.0 | — |
| (228) | 300 | 100.0 | — |
| (229) | 300 | 100.0 | — |
| (230) | 300 | 100.0 | — |
| (231) | 300 | 100.0 | — |
| (232) | 300 | 100.0 | — |
| (233) | 300 | 100.0 | — |
| (234) | 300 | 100.0 | — |
| (235) | 300 | 100.0 | — |
| (236) | 300 | 100.0 | — |
| (237) | 300 | 100.0 | — |
| (238) | 300 | 100.0 | — |
| (239) | 300 | 100.0 | — |
| (240) | 300 | 100.0 | — |
| (241) | 300 | 100.0 | — |
| (242) | 300 | 100.0 | — |
| (243) | 300 | 100.0 | — |
| (244) | 300 | 100.0 | — |
| (245) | 300 | 100.0 | — |
| (246) | 300 | 100.0 | — |
| (247) | 300 | 100.0 | — |
| (248) | 300 | 100.0 | — |
| (249) | 300 | 100.0 | — |
| (250) | 300 | 100.0 | — |
| (251) | 300 | 100.0 | — |
| (252) | 300 | 100.0 | — |
| (253) | 300 | 100.0 | — |
| (254) | 300 | 100.0 | — |
| (255) | 300 | 100.0 | — |
| (256) | 300 | 100.0 | — |
| (257) | 300 | 100.0 | — |
| (258) | 300 | 100.0 | — |
| (259) | 300 | 100.0 | — |
| (260) | 300 | 100.0 | — |
| (261) | 300 | 100.0 | — |
| (262) | 300 | 100.0 | — |
| (263) | 300 | 100.0 | — |
| (264) | 300 | 100.0 | — |
| (265) | 300 | 100.0 | — |
| (266) | 300 | 100.0 | — |
| (267) | 300 | 100.0 | — |
| (268) | 300 | 100.0 | — |
| (269) | 300 | 100.0 | — |
| (270) | 300 | 100.0 | — |
| (271) | 300 | 100.0 | — |
| (272) | 300 | 100.0 | — |
| (273) | 300 | 100.0 | — |
| (274) | 300 | 100.0 | — |
| (275) | 300 | 100.0 | — |
| (276) | 300 | 100.0 | — |
| (277) | 300 | 100.0 | — |
| (278) | 300 | 100.0 | — |
| (279) | 300 | 100.0 | — |
| (280) | 300 | 100.0 | — |
| (281) | 300 | 100.0 | — |
| (282) | 300 | 100.0 | — |
| (283) | 300 | 100.0 | — |
| (284) | 300 | 100.0 | — |
| (285) | 300 | 100.0 | — |
| (286) | 300 | 100.0 | — |
| (287) | 300 | 100.0 | — |
| (288) | 300 | 100.0 | — |
| (289) | 300 | 100.0 | — |
| (290) | 300 | 100.0 | — |
| (291) | 300 | 100.0 | — |
| (292) | 300 | 100.0 | — |
| (293) | 300 | 100.0 | — |
| (294) | 300 | 100.0 | — |
| (295) | 300 | 100.0 | — |
| (296) | 300 | 100.0 | — |
| (297) | 300 | 100.0 | — |
| (298) | 300 | 100.0 | — |
| (299) | 300 | 100.0 | — |
| (300) | 300 | 100.0 | — |
| (301) | 300 | 100.0 | — |
| (302) | 300 | 100.0 | — |
| (303) | 300 | 100.0 | — |
| (304) | 300 | 100.0 | — |
| (305) | 300 | 100.0 | — |
| (306) | 300 | 100.0 | — |
| (307) | 300 | 100.0 | — |
| (308) | 300 | 100.0 | — |
| (309) | 300 | 100.0 | — |
| (310) | 300 | 100.0 | — |
| (311) | 300 | 100.0 | — |
| (312) | 300 | 100.0 | — |
| (313) | 300 | 100.0 | — |
| (314) | 300 | 100.0 | — |
| (315) | 300 | 100.0 | — |
| (316) | 300 | 100.0 | — |
| (317) | 300 | 100.0 | — |
| (318) | 300 | 100.0 | — |
| (319) | 300 | 100.0 | — |
| (320) | 300 | 100.0 | — |
| (321) | 300 | 100.0 | — |
| (322) | 300 | 100.0 | — |
| (323) | 300 | 100.0 | — |
| (324) | 300 | 100.0 | — |
| (325) | 300 | 100.0 | — |
| (326) | 300 | 100.0 | — |
| (327) | 300 | 100.0 | — |
| (328) | 300 | 100.0 | — |
| (329) | 300 | 100.0 | — |
| (330) | 300 | 100.0 | — |
| (331) | 300 | 100.0 | — |
| (332) | 300 | 100.0 | — |
| (333) | 300 | 100.0 | — |
| (334) | 300 | 100.0 | — |
| (335) | 300 | 100.0 | — |
| (336) | 300 | 100.0 | — |
| (337) | 300 | 100.0 | — |
| (338) | 300 | 100.0 | — |
| (339) | 300 | 100.0 | — |
| (340) | 300 | 100.0 | — |
| (341) | 300 | 100.0 | — |
| (342) | 300 | 100.0 | — |
| (343) | 300 | 100.0 | — |
| (344) | 300 | 100.0 | — |
| (345) | 300 | 100.0 | — |
| (346) | 300 | 100.0 | — |
| (347) | 300 | 100.0 | — |
| (348) | 300 | 100.0 | — |
| (349) | 300 | 100.0 | — |
| (350) | 300 | 100.0 | — |
| (351) | 300 | 100.0 | — |
| (352) | 300 | 100.0 | — |
| (353) | 300 | 100.0 | — |
| (354) | 300 | 100.0 | — |
| (355) | 300 | 100.0 | — |
| (356) | 300 | 100.0 | — |
| (357) | 300 | 100.0 | — |
| (358) | 300 | 100.0 | — |

TABLE 8-continued

| Test compound | Dosage rate of active ingredient (g/10 are) | Percentage of healthy seedlings (%) | Phytotoxicity |
|---|---|---|---|
| (359) | 300 | 100.0 | — |
| (360) | 300 | 100.0 | — |
| (361) | 300 | 100.0 | — |
| (362) | 300 | 100.0 | — |
| (363) | 300 | 100.0 | — |
| (364) | 300 | 100.0 | — |
| (365) | 300 | 100.0 | — |
| (366) | 300 | 100.0 | — |
| (367) | 300 | 100.0 | — |
| (368) | 300 | 100.0 | — |
| (369) | 300 | 100.0 | — |
| (370) | 300 | 100.0 | — |
| (371) | 300 | 100.0 | — |
| (372) | 300 | 100.0 | — |
| (373) | 300 | 100.0 | — |
| (374) | 300 | 100.0 | — |
| B | 15.0 (1/10) a) | 73.3 | — |
| Inoculated and untreated plot | — | 6.7 | — |
| Uninoculated and untreated plot | — | 100.0 | — |

TEST EXAMPLE 3

Controlling Effect Against Fusarium Wilt of Cucumber (*Fusarium oxysporum* f.sp. *cucmerinum*)

A plastic pot was filled with field soil and then with a uniform mixture of infested soil containing cultured *Fusarium oxysporum* f.sp. *cucumerinum* and a prescribed amount of each test compound in the form of dust prepared according to Formulation example 1 until the upper surafce of the soil reached a level of 5 cm. In this test, as to hydroxyisoxazole, its prescribed amount was diluted with water and applied to drench the pot filled with the field soil. The seed of cucumber (variety, Shimoshirazuchibai) was sowed at a rate of 10/pot and covered with soil. After three weeks' cultivation in a greenhouse, the controlling effect was examined.

The results are shown in Table 9.

TABLE 9

| Test compound | Dosage rate of active ingredient (g/10 are) | Percentage of healthy seedlings (%) | Phytotoxicity |
|---|---|---|---|
| (2) | 300 | 100.0 | — |
| (4) | " | 100.0 | — |
| (5) | " | 100.0 | — |
| (61) | " | 100.0 | — |
| (123) | " | 100.0 | — |
| (217) | " | 100.0 | — |
| (221) | " | 100.0 | — |
| (280) | " | 100.0 | — |
| (349) | " | 100.0 | — |
| (353) | " | 100.0 | — |
| C | 600 | 53.3 | — |
| Inoculated and untreated plot | — | 3.3 | — |
| Uninoculated and untreated plot | — | 100.0 | — |

TEST EXAMPLE 4

Controlling Effect Against Fusarium Wilt of Tomato (*Fusarium oxysporum* f.sp. *lycopersici*)

Each test compound in the form of emulsifiable concentrate formulated according to Formulation example 4 was diluted with water to a prescribed concentration and sprayed on tomato seedlings (variety, Fukuju No. 2) in the three-leaf stage cultivated in a plastic pot so that the spray liquor was thoroughly attached to the leaf surface. After spraying, the seedlings were inoculated by drenching their root with the spore suspension of *Fusarium oxysporum* f.sp. *lycopersici*. After inoculation, the seedlings were cultivated for three weeks in a greenhouse, and the controlling effect was examined.

The results are shown in Table 10.

TABLE 10

| Test compound | Dosage rate of active ingredient (g/10 are) | Percentage of healthy seedlings (%) | Phytotoxicity |
|---|---|---|---|
| (2) | 1000 | 100.0 | — |
| (4) | " | 100.0 | — |
| (5) | " | 100.0 | — |
| (52) | " | 100.0 | — |
| (61) | " | 100.0 | — |
| (91) | " | 100.0 | — |
| (123) | " | 100.0 | — |
| (217) | " | 100.0 | — |
| (221) | " | 100.0 | — |
| (280) | " | 100.0 | — |
| (349) | " | 100.0 | — |
| (353) | " | 100.0 | — |
| (367) | " | 100.0 | — |
| A | " | 53.3 | — |
| Inoculated and untreated plot | — | 13.3 | — |
| Uninoculated and untreated plot | — | 100.0 | — |

TEST EXAMPLE 5

Controlling Effect Against Verticillium Wilt of Eggplant (*Verticillium albo-atrum*)

Soil in a plot (2 m$^2$) was inoculated with 100 g of a wheat bran medium containing cultured *Verticillium albo-atrum*, and then mixed with a prescribed amount of each test compound in the form of fine granule formulated according to Formulation example 5. In this test, chloropicrin was used as follows: After innoculation with the pathogen, a prescribed amount of chloropicrin was injected into the soil which was then covered with a polyvinyl chloride film and allowed to stand for one week; thereafter, the film was removed, the soil was ploughed and gas release was carried out for further one week. Thereafter, an eggplant seedling (variety, Senryo No. 2) in the two-leaf stage was transplanted at a rate of 16/plot and cultivated for about six seeks in a greenhouse, and the controlling effect was examined.

The results are shown in Table 11.

TABLE 11

| Test compound | Dosage rate of active ingredient (g/10 are) | Percentage of healthy seedlings (%) | Phytotoxicity |
|---|---|---|---|
| (2) | 1000 | 93.8 | — |
| (4) | " | 97.9 | — |
| (5) | " | 93.8 | — |
| (60) | " | 95.8 | — |
| (61) | " | 91.7 | — |
| (123) | " | 92.1 | — |
| (289) | " | 96.6 | — |
| (217) | " | 92.1 | — |
| (221) | " | 94.3 | — |
| (349) | " | 90.8 | — |
| B | 30.0 (1/10 a) | 54.2 | — |
| Inoculated and untreated plot | — | 10.4 | — |
| Uninoculated and untreated plot | — | 100.0 | — |

TEXT EXAMPLE 6

Controlling Effect Against Club-Root of Chinese Cabbage (*Plasmodiophora barassicae*)

A plastic pot was filled with field soil and then with a uniform mixture of a soil infested with *Plasmodiophora brassicae* and a prescribed amount of each test compound in the form of dust formulated according to Formulation example 1 until the upper surface of the soil reached a leve of 5 cm. Thereafter, the seed of chinese cabbage (variety, Taibyo-60 nichi) was sowed at a rate of 15/pot and covered with soil. After four weeks' cultivation in a greenhouse, the controlling effect was examined.

The results are shown in Table 12.

TABLE 12

| Test compound | Dosage rate of active ingredient (g/10 are) | Percentage of healthy seedlings (%) | Phytotoxicity |
| --- | --- | --- | --- |
| (2) | 1000 | 93.8 | — |
| (4) | " | 93.8 | — |
| (5) | " | 83.3 | — |
| (52) | " | 85.4 | — |
| (61) | " | 89.6 | — |
| (91) | " | 92.1 | — |
| (123) | " | 81.6 | — |
| (217) | " | 83.9 | — |
| (219) | " | 87.5 | — |
| (220) | " | 91.3 | — |
| (221) | " | 89.7 | — |
| (279) | " | 81.2 | — |
| (349) | " | 85.2 | — |
| (353) | " | 90.4 | — |
| D | 2000 | 72.9 | — |
| Inoculated and untreated plot | — | 8.9 | — |
| Uninoculated and untreated plot | — | 100.0 | — |

TEST EXAMPLE 7

Controlling Effect Against Fusarium Wilt of Cotton (*Fusarium oxysporum* f.sp. *vasinfectum*)

A plastic pot was filled with field soil and infested soil containing cultured *Fusarium oxysporum* f.sp. *vasinfectum*, and the seed of cotton (variety, Coker) dressed with a prescribed amount of each test compound in the form of wettable powder formulated according to Formulation example 3 was sowed at a rate of 10/pot and covered with soil. After three weeks' cultivation in a greenhouse, the controlling effect was examined.

The results are shown in Table 13.

TABLE 13

| Test compound | Amount of active ingredient weight of dry seed (g/kg) | Percentage of healthy seedlings (%) | Phytotoxicity |
| --- | --- | --- | --- |
| (91) | 4 | 100.0 | — |
| (217) | " | 100.0 | — |
| (219) | " | 100.0 | — |
| (221) | " | 100.0 | — |
| (247) | " | 100.0 | — |
| Inoculated and untreated plot | — | 9.7 | — |
| Uninoculated and untreated plot | — | 100.0 | — |

What is claimed is:

1. A 2-cycloalkenylamine derivative represented by the formula,

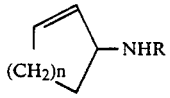

wherein R represents a $C_{1-5}$ lower alkyl group substituted by cyano.

2. The compound according to claim 1 wherein R is $CH(CH_3)CN$.

3. A 2-cycloalkenylamine derivative represented by the formula,

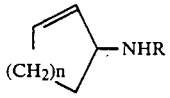

wherein R represents a $C_{1-2}$ alkyl group which is substituted wth a $C_{2-3}$ alkoxycarbonyl group, and n represents 2 or 3.

* * * * *